US011980692B2

(12) United States Patent
Guha et al.

(10) Patent No.: US 11,980,692 B2
(45) Date of Patent: *May 14, 2024

(54) PROCESS FOR PREPARING A COATED HARD SHELL CAPSULE

(71) Applicant: Evonik Operations GmbH, Essen (DE)

(72) Inventors: Ashish Guha, Mumbai (IN); Vishal Kaneria, Navi Mumbai (IN); Vinay Jain, Mumbai (IN); Shraddha Joshi, Thane (IN); Miriam Robota, Dietzenbach (DE); Felix Hofmann, Darmstadt (DE); Marcel Arndt, Moerfelden-Walldorf (DE); Hans Bär, Michelstadt (DE)

(73) Assignee: Evonik Operations GmbH, Essen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/733,083

(22) PCT Filed: Nov. 14, 2018

(86) PCT No.: PCT/EP2018/081204
§ 371 (c)(1),
(2) Date: May 13, 2020

(87) PCT Pub. No.: WO2019/096833
PCT Pub. Date: May 23, 2019

(65) Prior Publication Data
US 2021/0361585 A1    Nov. 25, 2021

(30) Foreign Application Priority Data
Nov. 17, 2017  (IN) .............................. 201731041169

(51) Int. Cl.
A61K 9/48    (2006.01)

(52) U.S. Cl.
CPC .......... *A61K 9/4891* (2013.01); *A61K 9/4808* (2013.01); *A61K 9/4816* (2013.01)

(58) Field of Classification Search
CPC ... A61K 9/4891; A61K 9/4808; A61K 9/4816
See application file for complete search history.

(56) References Cited

U.S. PATENT DOCUMENTS

| | | | |
|---|---|---|---|
| 9,107,451 B2 | 8/2015 | Skalsky et al. | |
| 10,682,307 B2 | 6/2020 | Engel et al. | |
| 11,266,605 B2* | 3/2022 | Bravo Gonzaléz | .. A61K 9/4825 |
| 2011/0033530 A1 | 2/2011 | Skalsky et al. | |
| 2011/0097397 A1 | 4/2011 | Wang et al. | |
| 2014/0079792 A1* | 3/2014 | Schattka | ............... A61K 9/5026 514/263.36 |
| 2017/0119681 A1* | 5/2017 | Bravo Gonzaléz | .. A61K 9/4891 |
| 2019/0282493 A1 | 9/2019 | Engel et al. | |
| 2022/0142929 A1 | 5/2022 | Hölzer et al. | |
| 2023/0088952 A1 | 3/2023 | Jain et al. | |

FOREIGN PATENT DOCUMENTS

| | | |
|---|---|---|
| EP | 3 646 857 | 5/2020 |
| JP | S49-30524 | 3/1974 |
| JP | S61-221117 | 10/1986 |
| JP | S63-23172 | 5/1988 |
| JP | 2003-325642 | 11/2003 |
| JP | 2014-517018 | 7/2014 |
| WO | 2007/070052 A2 | 6/2007 |
| WO | 2007/070052 A3 | 6/2007 |
| WO | 2011012369 | 2/2011 |
| WO | 2011/151722 A2 | 12/2011 |
| WO | 2011/151722 A3 | 12/2011 |
| WO | 2013/170012 A2 | 11/2013 |
| WO | 2013/170012 A3 | 11/2013 |
| WO | 2017/120592 | 7/2017 |
| WO | 2020/182611 | 9/2020 |
| WO | 2020/229178 | 11/2020 |
| WO | 2020/229192 | 11/2020 |

OTHER PUBLICATIONS

International Search Report dated Feb. 25, 2019 in PCT/EP2018/081204.
Written Opinion dated Feb. 25, 2019 in PCT/EP2018/081204.
European Search Report dated Jul. 10, 2018 in European Application No. 18151993.5.
Chinese Office Action dated Jan. 5, 2022 in Chinese Patent Application No. 201880086513.5, with English translation.
U.S. Office Action dated Apr. 20, 2022 in U.S. Appl. No. 17/595,145, 11 pages.
Japanese Office Action dated Jul. 29, 2022, in Japanese Application No. 2020-0526937, with English translation, 8 pages.
Japanese Office Action dated Mar. 8, 2023, in Japanese Application No. 2020-526937, with English translation, 9 pages.
Bar et al., U.S. Appl. No. 18/563,517, filed Nov. 22, 2023.
Bar et al., U.S. Appl. No. 18/563,327, filed Nov. 21, 2023.
U.S. Appl. No. 18/563,517, filed Nov. 22, 2023, Bär et al.
U.S. Appl. No. 18/563,327, filed Nov. 21, 2023, Bär et al.
U.S. Office Action dated Sep. 28, 2023, in U.S. Appl. No. 18/054,741, 12 pages.
U.S. Appl. No. 18/054,741, filed Nov. 11, 2022, 2023/0088952, Jain et al.

(Continued)

*Primary Examiner* — Robert A Wax
*Assistant Examiner* — Olga V. Tcherkasskaya
(74) *Attorney, Agent, or Firm* — Grüneberg and Myers PLLC

(57) ABSTRACT

A process prepares a polymer-coated hard shell capsule, suitable as container for pharmaceutical or nutraceutical biologically active ingredients. The hard shell capsule can include a body and a cap. In the closed state, the cap overlaps the body either in a pre-locked state or in a final-locked state. The hard shell capsule can be provided in the pre-locked state and spray-coated with a coating solution, suspension, or dispersion that includes a polymer or a mixture of polymers to create a coating layer which covers the outer surface of the hard shell capsule in the pre-locked state.

8 Claims, 4 Drawing Sheets

(56) References Cited

OTHER PUBLICATIONS

U.S. Office Action dated Jul. 6, 2023, in U.S. Appl. No. 17/438,886, 14 pages.
U.S. Appl. No. 17/438,886, filed Sep. 13, 2021, 2022/0142929, Hölzer et al.

* cited by examiner

US 11,980,692 B2

PROCESS FOR PREPARING A COATED HARD SHELL CAPSULE

CROSS-REFERENCE TO RELATED APPLICATIONS

This application is a National Stage entry under § 371 of International Application No. PCT/EP2018/081204, filed on Nov. 14, 2018, and which claims the benefit of Indian Application No. 201731041169, filed on Nov. 17, 2017, the contents of both of which are hereby incorporated by reference in their entireties.

BACKGROUND OF THE INVENTION

FIELD OF THE INVENTION

The invention is in the field of processes for preparing polymer-coated hard shell capsules.

DISCUSSION OF THE BACKGROUND

U.S. Pat. No. 4,138,013 describes hard shell capsules with enteric properties. The hard shell capsules comprise telescopically engaged body and cap portions. The capsule body and cap portions are formed by dip-molding using homogeneous film-forming mixt comprising selected from hydroxypropyl methyl cellulose (HPMC), a mixture of (1) hydroxypropyl methyl cellulose and an ammonium salt of cellulose acetate phthalate or (2) gelatin and an ammonium salt of a copolymer of (meth)acrylic acid and methacrylic acid alkyl ester. The capsules itself have already enteric properties without applying a further enteric coating layer.

Huyghebaert et al., *European Journal of Pharmaceutical Sciences* 21 (2004) 617-623, describe an alternative method for the enteric coating of capsules made of HPMC in which ready-to-use enteric capsule parts are obtained. It is reported that, in contrast to gelatine capsules, HPMC capsules can be enteric coated relatively easily from aqueous preparations. However, it is necessary to additionally apply a sealing between the capsule halves, e.g. through a gelatine solution to be applied manually, in order to avoid a leakage of the capsule and an uncontrolled escape of the contents in the stomach. Another technique is to apply water/ethanol mixtures between the capsule halves and to weld the parts together at 40-60° C.

Using aqueous preparations (EUDRAGIT® FS 30 D, EUDRAGIT® L 30 D-55, Aquoat® AS-HF or Sureteric®) based on (meth)acrylate copolymers or polyvinyl acetate phthalate, plasticizers such as triethyl citrate and further auxiliaries, such as, for example, talc, it is possible to provide HPMC capsules with an enteric film from separately coated bodies and caps. A separate sealing step can be prevented in the case of this coating technology. In particular, HPMC capsules which have been coated with (meth) acrylate copolymers are depicted as particularly advantageous in the sum of their properties.

WO 2011/012369A1 describes a coating composition for the enteric coating of capsule halves made of water-soluble or water-swellable polymer material.

US 859027862 describes a method for fluid-tight sealing of filled medicament capsules. The capsule parts are filled with a gas that is at a different temperature or pressure or both than the temperature or pressure or both outside the capsule. The capsule parts are fitted together such that a differential pressure reduction in the capsule body and the capsule cap results. A leak-tight seal is provided in the gap between the capsule body and the capsule cap, wherein the gap is around 20 to 50 microns.

US 20170035699A1 describes an acid-resistant banding solution for acid resistant two piece hard capsules.

WO 2015/177028 describes a capsule containing a non-liquid fill and comprising a modified release characterized in that the capsule is band sealed below the modified release coating. The modified release coating may be a delayed release coating or a controlled release coating, which may be an enteric coating. Film forming agents for the enteric coating may be selected from anionic (meth)acrylate copolymers or anionic celluloses. The coating amount may be in the range from about 2 to 12 mg per $cm^2$ of the relevant capsule surface area. Before the coating is applied onto the readily filled and closed capsules, the gap between body and cap is sealed with a band to prevent leakage.

WO2013/1710012A2, WO2007/070052A2, WO2011/151722A2 and WO2017/120592A1 contain examples wherein hard shell capsules are filled with active ingredient containing powder formulations, are closed and subsequently coated with enteric (meth)acrylate copolymers.

BRIEF DESCRIPTION OF DRAWINGS

FIG. 1a) shows an example for a capsule comprising body and cap separately FIG. 1b) shows the body and cap in the pre-locked state FIG. 1c) shows the body and the cap in the final-locked state
1=Body
11=Encircling notch
12=Tapered rim
2=Cap
21=Encircling notch
22=Elongated dimples
FIG. 2

Figure 3:
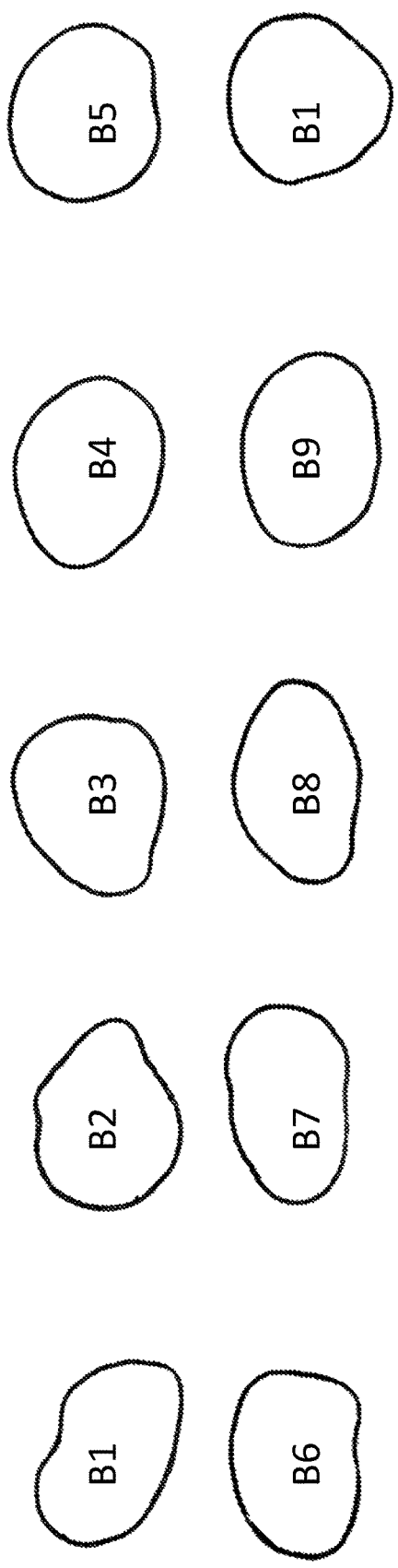

Body: length=16.61 mm, cylinder (length of the cylindrical part)=13.29 mm, outer diameter=6.63 mm
Cap: length=9.78 mm, cylinder (length of the cylindrical part)=6.32 mm, outer diameter=6.91 mm
FIG. 3

FIG. 3 refers to the comparative example C4, where bodies and caps were separately spray-coated with a polymer. FIG. 3 shows the microscopic images of the open side, respectively of the rim line of ten randomly chosen bodies from the spray coating process, numbered B1 to B10. The images were recorded and reduced to black and white images for giving a clear reproduction. As shown in the pictures B1 to B10, the process of separate coating of the bodies leads to different kinds of deformation of the originally round rims.

FIG. 4

Figure 4:
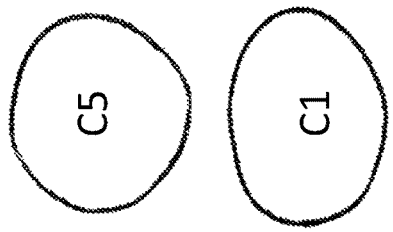
Figure 4:
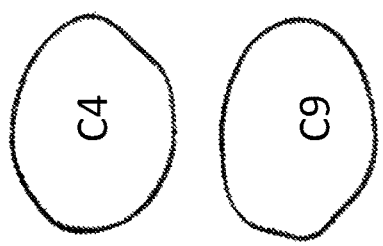
Figure 4:
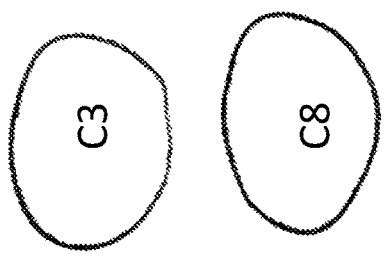
Figure 4:
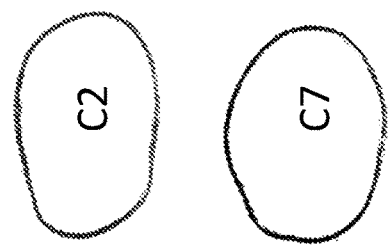
Figure 4:
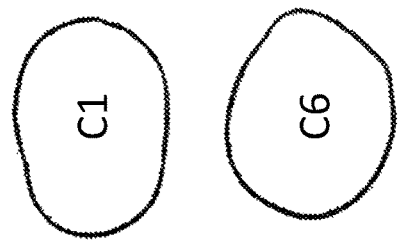

FIG. 4 refers to the comparative example C4, where bodies and caps were separately spray-coated with a polymer. FIG. 4 shows the microscopic images of the open side, respectively of the rim line of ten randomly chosen caps from the spray coating process, numbered C1 to C10. The images were recorded and reduced to black and white images for giving a clear reproduction. As shown in the pictures C1 to C10, the process of separate coating of the caps leads to different kinds of deformation of the originally round rims.

SUMMARY OF THE INVENTION

The invention is concerned with a process for preparing a polymer-coated hard shell capsule, suitable as container for pharmaceutical or nutraceutical biologically active ingredients, wherein the hard shell capsule is comprising a body and a cap, wherein in the closed stage the cap overlaps the body either in a pre-locked state or in a final-locked state, wherein the hard shell capsule is provided in the pre-locked state and spray-coated with a coating solution or dispersion comprising a polymer or a mixture of polymers to create a coating layer which covers the outer surface of the hard shell capsule in the pre-locked state. The invention is also concerned with polymer-coated hard shell capsule obtained from the process as described and with a pharmaceutical or nutraceutical dosage form comprising the polymer-coated hard shell capsule in the final-locked stage containing a fill comprising a pharmaceutical or nutraceutical biologically active ingredient.

In Huyghebaert et al., *European Journal of Pharmaceutical Sciences* 21 (2004) 617-623, describes the separate coating of bodies and caps of hard shell capsules with certain polymers. The bodies and caps can be filled with an active ingredient and show no leakage in release tests. There is also no need of additional banding. A disadvantage of this method is however that the separately polymer-coated bodies and caps must be subsequently filled and closed manually. Since bodies and caps often have tolerances, matching bodies and caps have to be manually selected. Furthermore, the previous form of the uncoated bodies and caps may suffer from the coating process in that their round form may be distorted. Thus, the percentage of out-of-specification parts is usually increased; meaning caps and bodies separately coated do not readily fit to each other. Therefore, fitting caps and bodies need to be manually selected, which requires multiple iteration and is not a first time right process. The need of manual processing limits the large scale industrial application.

Conventional capsule filling machines are designed to process uncoated capsules in the pre-locked state by opening, filling with an active ingredient or active ingredient containing composition and closing to the final-locked state. However, no conventional machines seem to exist that could process separately polymer-coated bodies and caps. Thus, specific designed machines would have to be designed and build. These machines would also have to cope with the problem of increased percentage of distorted roundness of separately coated bodies and caps, which might cause technical efforts on a high level.

Thus, there is a need for a polymer coating process for hard shell capsules that avoids the need of additional banding of the closed capsules and that results in tightly closed capsules without unwanted leakage of active ingredient. The problem of distorted roundness of bodies and caps by a polymer coating process that may occur when bodies and caps are separately polymer-coated should be avoided. The process should be suitable for involving conventional capsule filling machines.

In comparison to the separate coating as described in Huyghebaert et al., *European Journal of Pharmaceutical Sciences* 21 (2004) 617-623, the described process has the advantage that only one coating process is necessary. No coating material is sprayed inside the capsule halves. Thus, the loss of expensive coating solution or dispersion is significantly less. It was found that when the capsules are used in the pre-locked state there is no or almost no distortion of the roundness of the body and the cap. This modified capsule shape stability is maybe related to a stabilizing effect of the two capsule halves at the overlap area in the pre-locked state. Thus, the pre-locked state provides sufficient mechanical stability during the coating and drying process in conventional coating equipment like fluidized bed coater and drum coater. Furthermore, no selection of matching bodies and caps have to be done since the pre-locked delivered capsule parts, body and cap, already match each other. As a consequence of the improvements, the polymer-coated capsules in the pre-locked state can be further processed by conventional capsule filling machines. Thus, the pre-locked coated capsules are suitable as a part of large scale industrial production, e.g. coated capsules in the pre-locked state opening, filling with an active ingredient or active ingredient containing composition and closing into the final-locked state, of pharmaceutical or nutraceutical dosage forms comprising a polymer-coated hard shell capsule in the final-locked stage containing a fill comprising a pharmaceutical or nutraceutical biologically active ingredient.

It was surprisingly found that hard shell capsules coated in the inventive process are tightly closed and show no leakage although only a part of the overlapping area between body and cap is sealed by a coating. The described process is especially useful for providing tightly final-locked polymer-coated hard shell capsules for pharmaceutical or nutraceutical dosage forms with gastric resistance and an intended rapid release in the small intestine. The described process is also useful for providing polymer-coated hard shell capsules and pharmaceutical or nutraceutical dosage forms based on these kind of capsules with improved moisture protection properties, especially with decreased moisture up-take during storage.

The term a polymer or a mixture of polymers shall be understood as one polymer or a mixture of two or more polymers, for instance a mixture of two or three polymers. It is also possible that the coating layer may comprise or consist of several individual layers, maybe two layers with each containing a polymer or a polymer mixture, which may comprise the same or different polymers in the two or more layers. Preferably, the coating layer comprises or consists of only one coating layer. with preferably only one polymer or a mixture of two polymers. One polymer shall mean only one polymer or only one main polymer with the addition of negligible amounts of further polymers (5 or 2 or 1 or less % by weight calculated on the weight of the main polymer) that do not essentially influence the function of the main polymer. Negligible amounts of further polymers may be added for excipient functions such as improving the adhesion of the coating layer on the capsule material.

DETAILED DESCRIPTION OF THE INVENTION

Hard Shell Capsules

Hard shell capsules for pharmaceutical or nutraceutical purposes are well known to a skilled person. A hard shell capsule is a two-piece encapsulation capsule comprising of the two capsule halves, called the body and the cap. The capsule body and cap material is usually made from a hard and sometimes brittle material. The hard shell capsule comprises a body and a cap. Body and cap are usually of a one end open cylindrical form with closed rounded hemispherical ends on the opposite end. The shape and size of the cap and body are such that the body can be pushed telescopically with its open end into the open end of the cap.

The body and the cap comprise a potential overlapping matching area (overlap area) outside the body and inside the cap which partially overlap when the capsule is closed in the pre-locked stage and totally overlap in the final-locked stage. When the cap is partially slid over the overlapping matching area of the body the capsule is in the pre-locked stage. When the cap is totally slid over the overlapping matching area of the body the capsule is in the final-locked stage. The maintenance of the pre-locked stage or of the final-locked stage is usually supported by snap-in locking mechanisms of the body and the cap such as matching encircling notches or dimples, preferably elongated dimples.

Usually the body is longer than the cap. The outside overlapping area of the body can be covered by the cap in order to close or to lock the capsule. In the closed stage the cap covers the outside overlap area of the body either in a pre-locked state or in a final-locked state. In the final-locked state the cap covers the outside overlap area of the body in total, in the pre-locked state the cap overlaps the outside overlapping area of the body only partially. The cap can be slid over the body to be fixed in usually one of two different positions in which the capsule is closed either in a pre-locked state or in a final-locked state.

Hard shell capsules are commercially available in different sizes. Hard shell capsules are usually delivered as empty containers with the body and cap already positioned in the pre-locked state and on demand as separate capsules halves, bodies and caps. The pre-locked hard shell capsules can be provided to a capsule-filling machine, which performs the opening, filling and closing of the capsule into the final-locked state. Usually hard shell capsules are filled with dry materials, for instance with powders or granules comprising a biologically active ingredient.

The cap and body are provided with closure means that are advantageous for the pre-locking (temporary) and/or final locking of the capsule.

Therefore, elevated points may be provided on the inner wall of the cap and somewhat larger indented points are provided on the outer wall of the body, which are arranged so that when the capsule is closed the elevations fit into the indentations. Alternatively, the elevations may be formed on the outer wall of the body and the indentations on the inner wall of the cap. Arrangements in which the elevations or indentations arranged in a ring or spiral around the wall. Instead of the point-like configuration of the elevations and indentations, these may encircle the wall of the cap or body in an annular configuration, although advantageously recesses and openings are provided which enable an exchange of gases into and out of the capsule interior.

One or more elevations may be provided in an annular arrangement around the inner wall of the cap and the outer wall of the body such that, in the final-locked position of the capsule, an elevation on the cap is located adjacent to an elevation on the body. Sometimes elevations are formed on the outside of the body close to the open end and indentations are formed in the cap close to the open end such that the elevations on the body latch into the indentations in the cap in the final-locked position of the capsule. The elevations may be such that the cap can be opened in the pre-locked state at any time without damage to the capsule or, alternatively, so that once it has been closed the capsule cannot be opened again without destroying it.

Capsules with one or more such latching mechanisms (latches) (for example two encircling grooves) are preferred. More preferred are capsules with at least two such latching means which secure the two capsule parts to different degrees. In a part of this kind, a first latching (dimples or encirculating notches) means may be formed close to the openings in the capsule cap and the capsule body and a second latching (encircilating notches) can be shifted somewhat further towards the closed end of the capsule parts. The first latching means secure the two capsule parts less strongly than the second does. This variant has the advantage that after the production of the empty capsules the capsule cap and capsule body can initially be pre-locked joined together using the first latching mechanism. In order to fill the capsule the two capsule parts are then separated again. After filling, the two capsule parts are pushed together until the second set of latches firmly secures the capsule parts in a final-locked stage.

Preferably, the body and the cap of the hard shell capsule are comprising each encircling notches and/or dimples in the area, where the cap can be slid over the body. Encircling notches of the body and dimples of the cap match to each other to provide a snap-in or snap into-place mechanism. The dimples may be circular or elongated (oval) in the longitudinal direction.

Encircling notches of the body and encircling notches of the cap (closely matched rings) also match to each other to provide a snap-in or snap into-place mechanism. This allows the capsule to be closed by a snap-into-place mechanism either in a pre-locked state or in a final-locked state.

Preferably, matching encircling notches of the body and elongated dimples of the cap are used to fix the body and the cap to each other in the pre-locked state. Matching encircling notches of the body and the cap are preferably used to fix or lock the body and the cap to each other in the final-locked state.

The area, where the cap can be slid over the body may be called the overlapping area of the body and the cap or briefly the overlap area. If the cap overlaps the body only partially, maybe to 20 to 90 or 60 to 85% of the overlap area, the hard shell capsule is only partially closed (pre-locked). Preferably, in the presence of a locking mechanism, like matching encircling notches and/or dimples in body and cap, the partially closed capsule may be called pre-locked. When the capsule is polymer-coated in the pre-locked stage the coating will cover the completely outer surface including that part of the overlap area of the body and cap that is not overlapped by the cap in this pre-locked stage. When the capsule is polymer-coated in the pre-locked stage and then closed to the final-locked stage the coating of that part of the overlap area of the body and cap that was not overlapped by the cap in the pre-locked stage will then become covered by the cap. The presence of that part of the coating which is then enclosed in the final-locked stage between the body and the cap is sufficient for the hard shell capsule to be tightly sealed. This was not be no means to be foreseen.

If the cap overlaps the body the total overlapping area of the body, the hard shell capsule is finally closed or in the final-locked state. Preferably, in the presence of a locking mechanism, like matching encircling notches and/or dimples in body and cap, the finally closed capsule may be called final-locked.

Usually dimples are preferred for the fixing the body and the cap in the pre-locked state. As a non-binding rule the matching area of dimples is smaller than the matching area of encircling notches.

Thus snapped-in dimples may be snapped-out again by applying less forces than those that would be necessary to snap-out a snapped-in fixation by matching encircling notches.

The dimples of the body and cap are located in the area, where the cap can be slid over the body match to each other in the pre-locked state by a snap in or snap into-place mechanism. There may be for example 2, 4, or preferably 6 notches or dimples located distributed circular around the cap.

Usually the dimples of the cap are and the encircling notches of the body in the area, where the cap can be slid over the body match to each other so that they that allow the capsule to be closed by a snap-into-place mechanism in the pre-locked state. In the pre-locked state, the hard shell capsule can be re-opened manually or by a machine without damaging, because the forces needed to open are comparatively low. So the "pre-locked state" is sometimes designated also as "loosely capped".

Usually the encircling notches or matching locking rings of the body and the cap in the area, where the cap can be slid over the body match to each other so that they that allow the capsule to be closed by a snap-into-place mechanism in the final-locked state. In the final-locked state, the hard shell capsule cannot or can be only hardly be re-opened manually or by a machine without damaging, because the forces needed to open are comparatively high.

Usually dimples and the encircling notches are formed in the capsule body or capsule cap. When the capsule parts provided with these elevations and indentations are fitted into one another, ideally defined uniform gaps of from 10 microns to 150 microns, more particularly 20 microns to 100 microns, are formed along the contact surface between the capsule body and the capsule cap placed thereon.

Preferably, the body of the hard shell capsule comprises a tapered rim. The tapered rim prevent the rims of the body and the cap to collide and becoming damaged when the capsule is closed manually or by a machine.

In contrast to a hard shell capsule, a soft shell capsule is a welded one piece encapsulation capsule. A soft gel capsule is often made from blow molded soft gelling substances and is usually filled with liquids comprising a biologically active ingredient by injection. The invention is not concerned with welded soft shell one piece encapsulation capsules.

Sizes of Hard Shell Capsules

A closed, final-locked hard shell capsule may have a total length in the range from about 5 to 40 mm. The diameter of the cap may be in the range from about 4 to 12 mm. The diameter of the body may be in the range from about 2 to 11 mm. The length of the cap may be in the range from about 4 to 20 mm and that of the body in the range from 8 to 30 mm. The fill volume may be between about from 0.1 to 2 ml. The difference between the pre-locked length and the final-locked length may be about 1 to 5 mm.

Capsules can be divided into standardized sizes for example from sizes 000 to 5. A closed capsule of size 000 has, for example, a total length of about 28 mm with an outer diameter of the cap of about 9.9 mm and an outer diameter of the body of about 9.5 mm. The length of the cap is about 14 mm, that of the body about 22 mm. The fill volume is about 1.4 ml.

A closed capsule of size 5 has, for example, a total length of about 10 mm and an outer diameter of the cap of about 4.8 mm and an outer diameter of the body of about 4.6 mm. The length of the cap is about 5.6 mm, that of the body about 9.4 mm. The fill volume is about 0.13 ml.

A size 0 capsule may show a length of about 23 to 24 mm in the pre-locked stage and of about 20.5 to 21.5 mm in the final-locked stage. Thus, the difference between the pre-locked length and the final-locked length may be about 2 to 3 mm.

Coated Hard Shell Capsule

The invention is concerned with a polymer-coated hard shell capsule, obtained from the process as described herein.

Material of the Body and the Cap

The material of the body and the cap may be selected from hydroxypropyl methyl cellulose, starch, gelatin, pullulan and a copolymer of C1- to C4-alkylester of (meth)acrylic acid and (meth)acrylic acid. Preferred are hard shell capsules where body and cap are comprising or consisting of HPMC or gelatin, most preferred is HPMC because of its good adhesion properties for the polymer coating.

Polymer or Polymer Mixture Comprised in the Coating Layer

The polymer or polymer mixture comprised in the coating layer are preferably film-forming polymers and may be selected from the groups of anionic polymers, cationic polymers and neutral polymers or any mixtures thereof.

The selection of generic or specific polymer features or embodiments as disclosed herein can be combined without restriction with any other generic or specific selection of material or numerical features or embodiments as disclosed herein, such as capsule materials, capsule sizes, coating thicknesses, biologically active ingredients and any other features or embodiments as disclosed.

Anionic Polymers—Enteric Coating and Gastric Resistance

The described process is especially useful for providing tightly closed polymer-coated hard shell capsules for pharmaceutical or nutraceutical dosage forms with gastric resistance and an intended rapid release in the small intestine (enteric coating) or large intestine (colon targeting).

The polymer or polymer mixture comprised in the coating layer may be an anionic polymer selected from the groups of anionic (meth)acrylate copolymers, anionic polyvinyl polymers or copolymers and anionic celluloses.

The above mentioned anionic polymers are also called "enteric polymers". In the coating layer such polymers are capable of providing enteric protection to the capsule.

Enteric protection shall mean, when the capsule is in the final closed state and comprises a fill comprising a pharmaceutical or nutraceutical biologically active ingredient, less than 10% of the comprised biologically active ingredient will be released after 120 min in 0.1 HCl, pH 1.2. Most preferred after 120 min in 0.1 HCl pH 1.2 and subsequent change to a buffered medium of pH 6.8 about 80% or more of the comprised biologically active ingredient will be released after a total time of 165 min or 180 min.

Colon targeting shall mean, when the capsule is in the final closed state and comprises a fill comprising a pharmaceutical or nutraceutical biologically active ingredient, less than 10% of the comprised biologically active ingredient will be released after 120 min in 0.1 HCl, pH 1.2. Preferred after 120 min in 0.1 HCl pH 1.2 and subsequent change to a buffered medium of pH 6.8 about 80% or more of the comprised biologically active ingredient will be released after a total time of 165 min. Most preferred after 120 min in 0.1 HCl pH 1.2 and 60 min at a subsequent intermediate change to a buffered medium of pH 6.5 or 6.8 and subsequent final change to a buffered medium of pH 7.2 or pH 7.4 about 80% or more of the comprised biologically active ingredient will be released after a total time of 225 min or 240 min.

The dissolution test is performed according to the United States Pharmacopeia 40 (USP) chapter <711> utilizing USP Apparatus II with a paddle speed of 75 rpm. The test media temperature will be adjusted to 37+0.5° C. Samples will be taken at appropriate time points.

Anionic (Meth)Acrylate Copolymers

Preferably the anionic (meth)acrylate copolymer comprises 25 to 95, preferably 40 to 95, in particular 60 to 40, % by weight free-radical polymerized C1- to C12-alkyl esters, preferably C1- to C4-alkyl esters of acrylic or of methacrylic acid and 75 to 5, preferably 60 to 5, in particular 40 to 60% by weight (meth)acrylate monomers having an anionic group. The proportions mentioned normally add up to 100% by weight. However it is also possible in addition, without this leading to an impairment or alteration of the essential properties, for small amounts in the region of 0 to 10, for example 1 to 5, % by weight of further monomers capable of vinylic copolymerization, such as, for example, hydroxyethyl methacrylate or hydroxy-ethyl acrylate, to be present. It is preferred that no further monomers capable of vinylic copolymerization are present.

C1- to C4-alkyl esters of acrylic or methacrylic acid are in particular methyl methacrylate, ethyl methacrylate, butyl methacrylate, methyl acrylate, ethyl acrylate and butyl acrylate.

A (meth)acrylate monomer having an anionic group is, for example, acrylic acid, with preference for methacrylic acid.

Suitable anionic (meth)acrylate copolymers are those polymerized from of 40 to 60% by weight methacrylic acid and 60 to 40% by weight methyl methacrylate or 60 to 40% by weight ethyl acrylate (EUDRAGIT® L or EUDRAGIT® L 100 55 types).

EUDRAGIT® L is a copolymer polymerized from 50% by weight methyl methacrylate and 50% by weight methacrylic acid. The pH of the start of the specific active ingredient release in intestinal juice or simulated intestinal fluid can be stated to be at about pH 6.0.

EUDRAGIT® L 100-55 is a copolymer polymerized from 50% by weight ethyl acrylate and 50% by weight methacrylic acid. EUDRAGIT® L 30 D-55 is a dispersion comprising 30% by weight EUDRAGIT® L 100-55. The pH of the start of the specific active ingredient release in intestinal juice or simulated intestinal fluid can be stated to be at about pH 5.5.

Likewise suitable are anionic (meth)acrylate copolymers polymerized from 20 to 40% by weight methacrylic acid and 80 to 60% by weight methyl methacrylate (EUDRAGIT® S type). The pH of the start of the specific active ingredient release in intestinal juice or simulated intestinal fluid can be stated to be at about pH 7.0.

Suitable (meth)acrylate copolymers are polymerized from 10 to 30% by weight methyl methacrylate, 50 to 70% by weight methyl acrylate and 5 to 15% by weight methacrylic acid (EUDRAGIT® FS type). The pH at the start of the specific active ingredient release in intestinal juice or simulated intestinal fluid can be stated to be at about pH 7.0.

EUDRAGIT® FS is a copolymer polymerized from 25% by weight methyl methacrylate, 65% by weight methyl acrylate and 10% by weight methacrylic acid. EUDRAGIT® FS 30 D is a dispersion comprising 30% by weight EUDRAGIT® FS.

Suitable is a copolymer composed of
  20 to 34% by weight methacrylic acid and/or acrylic acid,
  20 to 69% by weight methyl acrylate and
  0 to 40% by weight ethyl acrylate and/or where appropriate
  0 to 10% by weight further monomers capable of vinylic copolymerization,
with the proviso that the glass transition temperature of the copolymer according to ISO 11357 2, subsection 3.3.3, is not more than 60° C. This (meth)acrylate copolymer is particularly suitable, because of its good elongation at break properties, for compressing pellets to tablets.

Suitable is a copolymer polymerized from
  20 to 33% by weight methacrylic acid and/or acrylic acid,
  5 to 30% by weight methyl acrylate and
  20 to 40% by weight ethyl acrylate and
  more than 10 to 30% by weight butyl methacrylate and where appropriate
  0 to 10% by weight further monomers capable of vinylic copolymerization,
  where the proportions of the monomers add up to 100% by weight,
with the proviso that the glass transition temperature of the copolymer according to ISO 11357 2, subsection 3.3.3 (midpoint temperature Tmg), is 55 to 70° C. Copolymers of this type are particularly suitable, because of its good mechanical properties, for compressing pellets to tablets.

The copolymer preferably consists essentially to exclusively of 90, 95 or 99 to 100% by weight of the monomers methacrylic acid, methyl acrylate, ethyl acrylate and butyl methacrylate in the ranges of amounts indicated above. However, it is possible, without this necessarily leading to an impairment of the essential properties, for small amounts in the range from 0 to 10, e.g. 1 to 5% by weight of further monomers capable of vinylic copolymerization additionally to be present, such as, for example, methyl methacrylate, butyl acrylate, hydroxyethyl methacrylate, vinylpyrrolidone, vinyl-malonic acid, styrene, vinyl alcohol, vinyl acetate and/or derivatives thereof.

Further suitable anionic (meth)acrylate copolymers may be so called core/shell polymers as described in WO 2012/171575A2 or 2012/171576A1. A suitable Core Shell polymer is a copolymer from a two stage emulsion polymerzation process with a core of 75% by weight comprising polymerized units of 30% by weight of ethyl acrylate and 70% by weight of methyl methacrylate and a shell of polymerized units comprising 25% by weight of polymerized from 50% by weight ethyl acrylate and 50% by weight methacrylic acid.

A suitable Core-Shell polymer may be a copolymer from a two stage emulsion polymerization process with a core with 70 to 80% by weight, comprising polymerized units of 65 to 75% by weight of ethyl acrylate and 25 to 35% by weight of methyl methacrylate, and a shell with 20 to 30% by weight, comprising polymerized units of 45 to 55% by weight ethyl acrylate and 45 to 55% by weight methacrylic acid.

Anionic Celluloses

Anionic celluloses may be selected from carboxymethyl ethyl cellulose and its salts, cellulose acetate phthalate (CAP), cellulose acetate succinate (CAS), cellulose acetate trimellitate (CAT), hydroxypropyl methyl cellulose phthalate (HPMCP, HP50, HP55), hydroxypropyl methyl cellulose acetate succinate (HPMCAS-LF, -MF, -HF).

Anionic Vinyl Copolymers

Anionic vinyl copolymers may be selected from unsaturated carboxylic acids other than acrylic acid or methacrylic acid as exemplified by polyvinylacetatephthalate or a copolymer of vinylacetate and crotonic acid (preferably at a ratio of 9:1).

Cationic Polymers—Moisture Protection

The described process is especially useful for providing polymer-coated hard shell capsules and pharmaceutical or nutraceutical dosage forms based on these kind of capsules with improved moisture protection properties, e.g. with decreased moisture up-take during storage. For this purpose a coating with a cationic polymer, preferably with cationic (meth)acrylate copolymer is suggested.

A suitable cationic (meth)acrylate copolymer comprised in the coating layer may be polymerized from monomers comprising C1- to C4-alkyl esters of acrylic or of methacrylic acid and an alkyl ester of acrylic or of methacrylic acid with a tertiary or a quaternary ammonium group in the alkyl group. The cationic, water-soluble (meth)acrylate copolymer may be polymerized partly or fully of alkyl from acrylates and/or alkyl methacrylates having a tertiary amino group in the alkyl radical. A coating comprising these kind of polymers may have the advantage of providing moisture protection to the hard shell capsule. Moisture protection shall be understood a reduced uptake of moisture or water during storage of the readily filled and final-locked capsules.

A suitable cationic (meth)acrylate copolymer may be polymerized from 30 to 80% by weight of C1-to C4-alkyl esters of acrylic or of methacrylic acid, and 70 to 20% by weight of alkyl(meth)acrylate monomers having a tertiary amino group in the alkyl radical.

The preferred cationic (meth)acrylate copolymer may be polymerized from 20-30% by weight of methyl methacrylate, 20-30% by weight of butyl methacrylate and 60-40% by weight of dimethylaminoethyl methacrylate (EUDRAGIT® E type polymer).

A specifically suitable commercial (meth)acrylate copolymer with tertiary amino groups is polymerized from 25% by weight of methyl methacrylate, 25% by weight of butyl methacrylate and 50% by weight of dimethylaminoethyl methacrylate (EUDRAGIT® E100 or EUDRAGIT® E PO (powder form)). EUDRAGIT® E 100 and EUDRAGIT® E PO are water-soluble below approx. pH 5.0 and are thus also gastric juice-soluble.

A suitable (meth)acrylate copolymer may be composed of 85 to 98% by weight of free-radical polymerized C1 to C4 alkyl esters of acrylic or methacrylic acid and 15 to 2% by weight of (meth)acrylate monomers with a quaternary amino group in the alkyl radical.

Preferred C1 to C4 alkyl esters of acrylic or methacrylic acid are methyl acrylate, ethyl acrylate, butyl acrylate, butyl methacrylate and methyl methacrylate.

Further suitable cationic (meth)acrylate polymers may contain polymerized monomer units of 2 trimethylammonium-ethyl methacrylate chloride or trimethylammonium-propyl methacrylate chloride.

An appropriate copolymer may be polymerized from 50 70% by weight of methyl methacrylate, 20 40% by weight of ethyl acrylate and 7 2% by weight of 2 trimethylammoniumethyl methacrylate chloride.

A specifically suitable copolymer is polymerized from 65% by weight of methyl methacrylate, 30% by weight of ethyl acrylate and 5% by weight of 2 trimethylammonium-ethyl methacrylate chloride (EUDRAGIT® RS).

A further suitable (meth)acrylate copolymer may be polymerized from 85 to less than 93% by weight of C1 to C4 alkyl esters of acrylic or methacrylic acid and more than 7 to 15% by weight of (meth)acrylate monomers with a quaternary amino group in the alkyl radical. Such (meth) acrylate monomers are commercially available and have long been used for release-slowing coatings.

A specifically suitable copolymer is polymerized from 60% by weight of methyl methacrylate, 30% by weight of ethyl acrylate and 10% by weight of 2 trimethyhammoniumethyl methacrylate chloride (EUDRAGIT® RL).

Neutral Polymers

Neutral polymers are defined as polymers which are polymerized from neutral monomers and less than 5, preferably less than 2% by weight or most preferred not all of monomers with ionic groups.

Suitable neutral polymers for the coating of the hard shell capsule are methacrylate copolymers, preferably copolymers of ethyl acrylate and methyl methacrylate like EUDRAGIT® NE or EUDRAGIT® NM, neutral celluloses, such as methyl-, ethyl- or proply ethers of cellulose, for instance hydroxypropyl cellulose, polyvinyl pyrrolidone, polyvinyl acetate or polyvinyl alcohol.

Neutral methacrylate copolymers are often useful in mixture with anionic (meth)acrylate copolymers.

Neutral methacrylate copolymers are polymerized from at least to an extent of more than 95% by weight, in particular to an extent of at least 98% by weight, preferably to an extent of at least 99% by weight, in particular to an extent of at least 99% by weight, more preferably to an extent of 100% by weight, of (meth)acrylate monomers with neutral radicals, especially C1- to C4-alkyl radicals.

Suitable (meth)acrylate monomers with neutral radicals are, for example, methyl methacrylate, ethyl methacrylate, butyl methacrylate, methyl acrylate, ethyl acrylate, butyl acrylate. Preference is given to methyl methacrylate, ethyl acrylate and methyl acrylate.

Methacrylate monomers with anionic radicals, for example acrylic acid and/or methacrylic acid, may be present in small amounts of less than 5% by weight, preferably not more than 2% by weight, more preferably not more than 1 or 0.05 to 1% by weight.

Suitable examples are neutral or virtually neutral (meth) acrylate copolymers polymerized from 20 to 40% by weight of ethyl acrylate, 60 to 80% by weight of methyl methacrylate and 0 to less than 5% by weight, preferably 0 to 2 or 0.05 to 1% by weight of methacrylic acid or acrylic acid.

Suitable examples are neutral or virtually neutral (meth) acrylate copolymers polymerized from 20 to 40% methyl methacrylate by weight of, 60 to 80% by weight of ethyl acrylate and 0 to less than 5% by weight, preferably 0 to 2 or 0.05 to 1% by weight of methacrylic acid or acrylic acid. (EUDRAGIT® NE or EUDRAGIT® NM type).

EUDRAGIT® NE and EUDRAGIT® NM are copolymers comprising free-radically polymerized units of 28 to 32% by weight of methyl methacrylate and 68 to 72% by weight of ethyl acrylate.

Preference is given to neutral or essentially neutral methyl acrylate copolymers which, according to WO 01/68767, have been prepared as dispersions using 1-10% by weight of a nonionic emulsifier having an HLB value of 15.2 to 17.3. The latter offer the advantage that there is no phase separation with formation of crystal structures by the emulsifier (EUDRAGIT® NM type).

According to EP 1 571 164 A2, corresponding, virtually neutral (meth)acrylate copolymers with small proportions of 0.05 to 1% by weight of monoolefinically unsaturated C3-C8-carboxylic acids can, however, also be prepared by emulsion polymerization in the presence of comparatively small amounts of anionic emulsifiers, for example 0.001 to 1% by weight.

Natural Polymers

Especially for nutraceutical dosage forms so called "natural polymer" coatings are preferred by many customers.

Natural polymer are based on a source from nature, plants, microorganisms or animals, but sometimes further chemically processed. Natural polymers for coatings may be selected from polymers such as starch, alginates or salts of alginates, preferably sodium alginate, pectin, shellac, zein, carboxymethyl-zein, modified starch, for instance EUDRAGUARD® Natural, marine sponge collagen, chitosan, gellan gum. Suitable polymer mixtures may comprise: Ethyl cellulose and pectin, modified starch (EUDRAGUARD® Natural) and alginate and/or pectin, shellac and alginate and/or pectin, shellac and inulin, whey protein and gums (such as guar gum or tragacanth gum), zein and polyethylene glycol, sodium alginate and chitosan.

Coating Layer

The hard shell capsule is coated with a coating layer comprising the polymer or polymer mixtures as disclosed and optionally excipients, preferably pharmaceutical or nutraceutical acceptable excipients.

The coating layer may comprise 10% or more, 20% or more, 30% or more, 40% or more, 50% or more, 60% or more, 70% or more, 80% or more, 90% or more by weight or 100% by weight of the polymer or polymer mixture as disclosed herein. The coating layer may comprise 10-100, 10-90, 12-80, 15-70, 18-60 or 20-50% by weight of the polymer as disclosed herein.

The coating layer may optionally comprise up to 10, up to 20, up to 30, up to 40, up to 50, up to 60, up to 70, up to 80, up to 90% by weight of excipients, preferably pharmaceutical and/or nutraceutical excipients (pharmaceutically or nutraceutical acceptable excipients). The coating layer may comprise 0-100, 10-90, 20-88, 30-85, 40-82 or 50-80% by weight of excipients, preferably pharmaceutical and/or nutraceutical excipients. The polymer or polymer mixture and the optionally comprised pharmaceutical and/or nutraceutical excipients may add up to 100%.

Amount and Thickness of the Coating Layer

The amount of the coating layer (=total weight gain of the coating layer) applied should be sufficient to allow filling of the capillary between the outside overlapping area of the body covered by the cap. If the amount of coating layer applied is too low, this may result in no bridging or the bridging is too low. There may be not enough amount of coating layer between the body and the cap when the capsule is closed in the final-locked stage, which may result in insufficient tightness and leakage of the capsule.

For hard shell capsules, the amount of the coating layer should not be too high. If the amount of coating layer applied is too high this may result in difficulties to process the polymer-coated pre-locked hard shell capsules subsequently in a capsule-filling machine. If the amount of coating layer is less than 8 mg/cm$^2$, for instance 1 to 8 mg/cm$^2$ or 1 to 5 mg/cm$^2$ or 1 to 4 mg/cm$^2$ usually no problem with standard capsule-filling machines without modification will occur. In the range from 4 and up to about 8 mg/cm$^2$ capsule-filling machines can still be used, however the forms for the bodies and the caps should be adjusted to be somewhat wider. Such an adjustment can be easily performed by a mechanical engineer. Thus capsule-filling machines may be advantageously used within a range of an amount of coating layer from about 1 to about 8 mg/cm$^2$.

For a hard shell capsule of size #0, the amount of the coating layer should not be too high. If the amount of coating layer applied is too high this may result in difficulties to process the polymer-coated pre-locked hard shell capsules subsequently in a capsule-filling machine. If the amount of coating layer is less than 5 mg/cm$^2$, for instance 1 to 4 mg/cm$^2$ usually no problem with standard capsule-filling machines without modification will occur. In the range from 4 and up to about 8 mg/cm$^2$ capsule-filling machines can still be used, however the forms for the bodies and the caps should be adjusted to be somewhat wider. Such an adjustment can be easily performed by a mechanical engineer. Thus capsule-filling machines may be advantageously used within a range of an amount of coating layer from about 1 to about 8 mg/cm$^2$.

For a hard shell capsule of size #1, the amount of the coating layer should not be too high. If the amount of coating layer applied is too high this may result in difficulties to process the polymer-coated pre-locked hard shell capsules subsequently in a capsule-filling machine. If the amount of coating layer is less than 4 mg/cm$^2$, for instance 1 to 3.5 mg/cm$^2$ usually no problem with standard capsule-filling machines without modification will occur. In the range from 3.5 and up to about 8 mg/cm$^2$ capsule-filling machines can still be used, however the forms for the bodies and the caps should be adjusted to be somewhat wider. Such an adjustment can be easily performed by a mechanical engineer. Thus capsule-filling machines may be advantageously used within a range of an amount of coating layer from about 1 to about 8 mg/cm$^2$.

For a hard shell capsule of size #3, the amount of the coating layer should not be too high. If the amount of coating layer applied is too high this may result in difficulties to process the polymer-coated pre-locked hard shell capsules subsequently in a capsule-filling machine. If the amount of coating layer is less than 3 mg/cm$^2$, for instance 1 to 2.5 mg/cm$^2$ usually no problem with standard capsule-filling machines without modification will occur. In the range from 2.5 and up to about 6 mg/cm$^2$ capsule-filling machines can still be used, however the forms for the bodies and the caps should be adjusted to be somewhat wider. Such an adjustment can be easily performed by a mechanical engineer. Thus capsule-filling machines may be advantageously used within a range of an amount of coating layer from about 1 to about 6 mg/cm$^2$.

Above 8 mg/cm$^2$ and up to about 20 mg/cm$^2$ careful manual opening of the polymer-coated hard shell capsule, filling and closing to the pre-locked state may still be possible without causing damage to the polymer coating. If the coating layer is thicker than the gap between the uncoated body and the cap, the coated pre-locked capsules cannot be closed without damaging the applied coating as the cap can hardly slide over the body to the final-locked state anymore. The upper limit for manual closing of coated pre-locked hard shell capsules to the final-locked state without causing damage may be up to an amount of the coating layer of about 20 mg/cm$^2$. Above 20 mg/cm$^2$ even a very accurate and careful manual closing of the capsule may be no more possible without causing damage.

If the amount of coating layer applied is too high there will be also an assembly of too much coating layer at the rim of the cap where the gap between body and cap is in the pre-locked stage. This may result after drying in fissures of the coating layer when the coated pre-locked hard shell capsule is opened manually or in a machine. The fissures may result in a later leakage of the capsule. Finally, a too thick coating may result in difficulties or make it impossible to close the opened coated hard shell capsule to the final-locked stage since the coating layer is thicker than the gap in the overlapping area between the body and the cap.

As a rough rule the coating layer on the hard shell capsule may be applied in an amount (=a total weight gain) of 0.7 to 20, 1.0-18, 2 to 10, 4 to 8, 1.0 to 8, 1.5 to 5.5, 1.5 to 4 mg/cm$^2$.

As a rough rule the coating layer on the hard shell capsule may have an average thickness of about 5 to 100, 10 to 50, 15 to 75 μm.

As a rough rule the coating layer on the hard shell capsule may be applied in an amount of 5 to 50, preferably 8-40% dry weight in relation to the weight of the pre-locked capsule.

With this guidance a skilled person will be able to adjust the amounts of the coating layer in an range between too low and too high.

PREFERRED EMBODIMENTS

A first preferred embodiment discloses a
process for preparing a polymer-coated hard shell capsule, suitable as container for pharmaceutical or nutraceutical biologically active ingredients, wherein the hard shell capsule is comprising a body and a cap, wherein in the closed stage the cap overlaps the body either in a pre-locked state or in a final-locked state, wherein the hard shell capsule is provided in the pre-locked state and spray-coated with a coating solution or dispersion comprising a polymer or a mixture of polymers to create a coating layer which covers the outer surface of the hard shell capsule in the pre-locked state,
wherein the coating layer comprises
60 to 90, preferably 70 to 85% by weight of a polymer mixture and 10 to 40, preferably 15 to 30% by weight of pharmaceutical or nutraceutical acceptable excipients, comprising at least a plasticizer and an emulsifier, preferably glycerol monostearate (GMS), triethylcitrate (TEC) and polyoxyethylen(20)-sorbitanmonooleat (polysorbate 80),
wherein the polymer mixture and the pharmaceutical or nutraceutical acceptable excipients add up to 100%, wherein the polymer mixture comprises 60 to 90, preferably 70 to 85% by weight of a (meth)acrylate copolymers are polymerized from 10 to 30% by weight methyl methacrylate, 50 to 70% by weight methyl acrylate and 5 to 15% by weight methacrylic acid (EUDRAGIT® FS type) and 10 to 40, preferably 15 to 30% by weight of a (meth)acrylate copolymer polymerized from of 40 to 60% by weight methacrylic acid and 60 to 40% by weight ethyl acrylate (EUDRAGIT® L 100 55 type) and
wherein the amount of the coating layer (total weight gain) is from 1 to 8, preferably from 1 to 4 mg/cm².

The polymer-coated hard shell capsule of the first embodiment may be advantageously combined with a fill-in of the pharmaceutical active ingredients mesalamine or caffeine.

A second preferred embodiment discloses a
process for preparing a polymer-coated hard shell capsule, suitable as container for pharmaceutical or nutraceutical biologically active ingredients, wherein the hard shell capsule is comprising a body and a cap, wherein in the closed stage the cap overlaps the body either in a pre-locked state or in a final-locked state, wherein the hard shell capsule is provided in the pre-locked state and spray-coated with a coating solution or dispersion comprising a polymer or a mixture of polymers to create a coating layer which covers the outer surface of the hard shell capsule in the pre-locked state,
wherein the coating layer comprises
60 to 85, preferably 70 to 80% by weight of a polymer and 15 to 40, preferably 20 to 30% by weight of pharmaceutical or nutraceutical acceptable excipients, comprising at least a plasticizer and an emulsifier, preferably glycerol monostearate, triethylcitrate and polysorbate 80,
wherein the polymer and the pharmaceutical or nutraceutical acceptable excipients add up to 100%, wherein the polymer is a (meth)acrylate copolymer polymerized from of 40 to 60% by weight methacrylic acid and 60 to 40% by weight ethyl acrylate (EUDRAGIT® L 100 55 type) and
wherein the amount of the coating layer (total weight gain) is from 1 to 8, preferably from 1 to 4 mg/cm².

The polymer-coated hard shell capsule of the second embodiment may be advantageously combined with a fill-in of the pharmaceutical active ingredients metoprolol or omeprazole.

A third preferred embodiment discloses a
process for preparing a polymer-coated hard shell capsule, suitable as container for pharmaceutical or nutraceutical biologically active ingredients, wherein the hard shell capsule is comprising a body and a cap, wherein in the closed stage the cap overlaps the body either in a pre-locked state or in a final-locked state, wherein the hard shell capsule is provided in the pre-locked state and spray-coated with a coating solution or dispersion comprising a polymer or a mixture of polymers to create a coating layer which covers the outer surface of the hard shell capsule in the pre-locked state,
wherein the coating layer comprises
60 to 85, preferably 70 to 80% by weight of a polymer and 15 to 40, preferably 20 to 30% by weight of pharmaceutical or nutraceutical acceptable excipients, comprising at least a plasticizer and an emulsifier, preferably glycerol monostearate, triethylcitrate and polysorbate 80,
wherein the polymer and the pharmaceutical or nutraceutical acceptable excipients add up to 100%, wherein the polymer is a (meth)acrylate copolymers are polymerized from 10 to 30% by weight methyl methacrylate, 50 to 70% by weight methyl acrylate and 5 to 15% by weight methacrylic acid (EUDRAGIT® FS type) and
wherein the amount of the coating layer is from 1 to 8, preferably from 1 to 4 mg/cm².

The polymer-coated hard shell capsule of the third embodiment may be advantageously combined with a fill-in of the pharmaceutical active ingredients mesalamine or metoprolol.

Biologically Active Ingredient

The biologically active ingredient is preferably a pharmaceutical active ingredient and/or a nutraceutical active ingredient.

Pharmaceutical or Nutraceutical Active Ingredients

The invention is preferably useful for immediate, enteric or sustained release formulated pharmaceutical or nutraceutical dosage forms with a fill-in of pharmaceutical or nutraceutical active ingredients.

Suitable therapeutic and chemical classes of pharmaceutical active ingredients which members may be used as fill-in for the described polymer-coated hard shell capsules are for instance: analgesics, antibiotics or anti-infectives, antibodies, antiepileptics, antigens from plants, antirheumatics, benzimidazole derivatives, beta-blocker, cardiovascular drugs, chemotherapeutics, CNS drugs, digitalis glycosides, gastrointestinal drugs, e.g. proton pump inhibitors, enzymes, hormones, liquid or solid natural extracts, oligonucleotides, peptide hormones proteins, therapeutic bacteria, peptides, proteins (metal)salt i.e. aspartates, chlorides, orthates, urology drugs, vaccines Further examples of drugs that may be used as fill-in for the described polymer-coated hard shell capsules are for instance acamprosat, aescin, amylase, acetylsalicylic acid, adrenalin, 5-amino salicylic acid, aureomycin, bacitracin, balsalazine, beta carotene, bicalutamid, bisacodyl, bromelain, bromelain, budesonide, calcitonin, carbamacipine, carboplatin, cephalosporins, cetrorelix, clarithromycin, chloromycetin, cimetidine, cisapride, cladribine, clorazepate, cromalyn, 1-deaminocysteine-8-D-arginine-vasopressin, deramciclane, detirelix, dexlansoprazole, diclofenac, didanosine, digitoxin and other digitalis glycosides, dihydrostreptomycin, dimethicone, divalproex, drospirenone, duloxetine, enzymes, erythromycin, esomeprazole, estrogens, etoposide, famotidine, fluorides, garlic oil, glucagon, granulocyte colony stimulating factor (G-CSF), heparin, hydrocortisone, human growth hormon (hGH), ibuprofen, ilaprazole, insulin, Interferon, Interleukin, Intron A, ketoprofen, lansoprazole, leuprolidacetat lipase, lipoic acid, lithium, kinin, memantine, mesalazine, methenamine, milameline, minerals, minoprazole, naproxen, natamycin, nitrofurantion, novobiocin, olsalazine, omeprazole, orothates, pancreatin, pantoprazole, parathyroidhormone, paroxetine, penicillin, perprazol, pindolol, polymyxin, potassium, pravastatin, prednisone, preglumetacin progabide, pro-somatostatin, protease, quinapril, rabeprazole, ranitidine, ranolazine, reboxetine, rutosid, somatostatin streptomycin, subtilin, sulfasalazine, sulphanilamide, tamsulosin, tenatoprazole, thrypsine, valproic acid, vasopressin, vitamins, zinc, including their salts, derivatives, polymorphs, isomorphs, or any kinds of mixtures or combinations thereof.

It is evident to a skilled person that there is a broad overlap between the terms pharmaceutical and nutraceutical active ingredients, excipients and compositions respectively a pharmaceutical or a nutraceutical dosage form. Many substances listed as nutraceuticals may also be used as pharmaceutical active ingredients. Depending on the specific application and local authority legislation and classification, the same substance may be listed as a pharmaceutical or a nutraceutical active ingredient respectively a pharmaceutical or a nutraceutical composition or even both.

Nutraceuticals are well known to the skilled person. Nutraceuticals are often defined as extracts of foods claimed to have medical effects on human health. Thus, nutraceutical active ingredients may display pharmaceutical activities as well: Examples for nutraceutical active ingredients may be resveratrol from grape products as an antioxidant, soluble dietary fiber products, such as psyllium seed husk for reducing hypercholesterolemia, broccoli (sulphane) as a cancer preservative, and soy or clover (isoflavonoids) to improve arterial health. Thus, it is clear that many substances listed as nutraceuticals may also be used as pharmaceutical active ingredients.

Typical nutraceuticals or nutraceutical active ingredients that may be used as fill-in for the described polymer-coated hard shell capsules may also include probiotics and prebiotics. Probiotics are living microorganisms believed to support human or animal health when consumed. Prebiotics are nutraceuticals or nutraceutical active ingredients that induce or promote the growth or activity of beneficial microorganisms in the human or animal intestine.

Examples for nutraceuticals are resveratrol from grape products, omega-3-fatty acids or pro-anthocyanines from blueberries as antioxidants, soluble dietary fiber products, such as psyllium seed husk for reducing hypercholesterolemia, broccoli (sulphane) as a cancer preservative, and soy or clover (isoflavonoids) to improve arterial health. Other nutraceuticals examples are flavonoids, antioxidants, alpha-linoleic acid from flax seed, beta-carotene from marigold petals or antocyanins from berries. Sometimes the expression neutraceuticals or nutriceuticals are used as synonyms for nutraceuticals.

Preferred biologically actvie ingredients are metoprolol, mesalamine and omeprazole.

Excipients

Excipients are well known to a skilled person and often formulated along with the biologically active ingredient contained in the coated hard shell capsule and/or with the polymer coating of the hard shell capsule as disclosed and claimed herein. All excipients used must be toxicologically safe and be used in pharmaceuticals or nutraceuticals without risk for patients or consumers.

The dosage form may comprise excipients, preferably pharmaceutical or nutraceutical acceptable excipients, selected from the group of antioxidants, brighteners, binding agents, flavouring agents, flow aids, fragrances, glidants, penetration-promoting agents, pigments, plasticizers, emulsifier, pore-forming agents or stabilizers or combinations thereof. The pharmaceutically or nutraceutically acceptable excipients may be comprised in the core and/or in the coating layer comprising the polymer as disclosed. A pharmaceutical or nutraceutical acceptable excipient is an excipient, which is allowed to be used for the application in the pharmaceutical or nutraceutical field.

The coating layer may comprise up to 90, up to 80, up to 70, up to 50, up to 60, up to 50, up to 40, up to 30, up to 20, up to 10% by weight or not any (0%) excipients at all, respectively pharmaceutically or nutraceutically acceptable excipients. Preferably, except for polymer or polymer mixture of the coating layer, no further (excipient) polymers are present in the coating layer.

Plasticizers

The polymer coating of the hard shell capsule may comprise one or more plasticizers. Plasticizers achieve through physical interaction with a polymer a reduction in the glass transition temperature and promote film formation, depending on the added amount. Suitable substances usually have a molecular weight of between 100 and 20,000 and comprise one or more hydrophilic groups in the molecule, e.g. hydroxyl, ester or amino groups.

Examples of suitable plasticizers are alkyl citrates, glycerol esters, alkyl phthalates, alkyl sebacates, sucrose esters, sorbitan esters, diethyl sebacate, dibutyl sebacate, propylenglycol and polyethylene glycols 200 to 12,000. Preferred plasticizers are triethyl citrate (TEC), acetyl triethyl citrate (ATEC), diethyl sebacate and dibutyl sebacate (DBS). Mention should additionally be made of esters which are usually liquid at room temperature, such as citrates, phthalates, sebacates or castor oil. Esters of citric acid and sebacinic acid are preferably used. Glycerol monostearate (GMS) has plasticizing properties. In the sense of this disclosure glycerol monostearate (GMS), although it has some glidant properties as well and is sometimes designated as glidant, is regarded herein as a plasticizer.

Addition of the plasticizers to the formulation can be carried out in a known manner, directly, in aqueous solution or after thermal pre-treatment of the mixture. It is also possible to employ mixtures of plasticizers. However, since the polymer as disclosed herein shows a minimum film forming temperature (MFFT) of 35° C. or lower, it is possible to apply the polymer coating, for instance from an aqueous polymer dispersion, without the addition of a plasticizer. The polymer coating of the hard shell capsule may comprise one or more plasticizers, preferably up to 60, up to 30, up to 25, up to 20, up to 15, up to 10, up to 5, less than 5% by weight, calculated on the polymer or polymer mixture, of a plasticizer or any (0%) plasticizer at all may be comprised. Most preferred 20 to 30 by weight of mixture of glycerol monostearate (GMS) and triethlycitate, calculated on the polymer or polymer mixture, may be comprised in the coating layer.

Fillers

Standard fillers are usually added to the inventive formulation during processing to coating and binding agents. The quantities introduced and the use of standard fillers in pharmaceutical coatings or over layers is familiar to those skilled in the art. Examples of standard fillers are release agents, pigments, stabilizers, antioxidants, pore-forming agents, penetration-promoting agents, brighteners, fragrances or flavoring agents. They are used as processing adjuvants and are intended to ensure a reliable and reproducible preparation process as well as good long-term storage stability, or they achieve additional advantageous properties in the pharmaceutical form. They are added to the polymer formulations before processing and can influence the permeability of the coatings. This property can be used if necessary as an additional control parameter.

Glidants (Release Agents):

Glidants or release agents usually have lipophilic properties and are usually added to spray suspensions. They prevent agglomeration of cores during film formation. Suitable glidants are talc, Mg- or Ca-stearate, ground silica, kaolin or nonionic emulsifiers with an HLB value of between 2 and 8. Standard proportions for use of release agents in the inventive coating and binding agents range between 0.5 and 100% by weight relative to polymer.

In a particularly advantageous embodiment, the glidant or release agent is added in concentrated form as the outer layer. Application takes place in the form of powder or by spraying from aqueous suspension with 5 to 30% (weight/weight (w/w)) solid content. The necessary concentration is lower than for incorporation into the polymer layer and amounts to 0.1 to 2% by weight relative to the weight of the pharmaceutical form.

The coating layer of the dosage form may for instance comprise 20-80, preferably 30-70% by weight of the inventive polymer as disclosed and 20-80, 30-70% by weight of talc. The inventive polymer and talc may add up to 100% by weight.

Pigments

Only rarely a pigment is added in soluble form. As a rule pigments, such as aluminum oxide or iron oxide pigments are used in dispersed form. Titanium dioxide is used as a whitening pigment.

Standard proportions for use of pigments are between 10-200, 20-200% by weight relative to the polymer or polymer mixture in the coating layer. Proportions up to 200% by weight calculated on the polymer or polymer mixture can be easily processed.

In a particularly advantageous embodiment, the pigment is used directly in concentrated form as an additional outer layer a so called top coat. Application takes place in the form of powder or by spraying from aqueous suspension with 5 to 35% (w/w) solid content. The necessary concentration is lower than for incorporation into the polymer layer and amounts to 0.1 to 2% by weight relative to the weight of the pharmaceutical form.

Optional Top Coats and Sub Coats

Optionally the hard shell capsule may be additionally coated with a sub coat or a top coat or both.

A sub coat may be located between capsule and the coating layer, comprising the polymer or polymer mixture as disclosed. A sub coat has essentially no influence on the active ingredient release characteristics but may for instance improve the adhesion of the polymer coating layer. A sub coat is preferably essentially water-soluble, for instance it may consist of substances like HPMC as a film former. The average thickness of a sub coat layer is usually very thin, for example not more than 15 μm, preferably not more than 10 μm (0.1-0.6 mg/cm$^2$). A sub coat or a top coat has not necessarily to be applied on the hard shell capsule in the pre-locked state.

A top coat may be located onto the coating layer, comprising the polymer or polymer mixture as disclosed. A top coat is also preferably water-soluble or essentially water-soluble. A top coat may have the function of colouring the pharmaceutical or nutraceutical form or protecting from environmental influences for instance from moisture during storage. The top coat may consist out of a binder, for instance a water-soluble polymer like a polysaccharide or HPMC, or a sugar compound like saccharose. The top coat may further contain pharmaceutically or nutraceutically acceptable excipients like pigments or glidants in high amounts. The topcoat has essentially no influence on the release characteristics. A top coat may be applied on top of the pharmaceutical or nutraceutical dosage form comprising the polymer-coated hard shell capsule in the final-locked stage as described herein. The average thickness of a top coat layer is usually very thin, for example not more than 15 μm, preferably not more than 10 μm (0.1-0.6 mg/cm$^2$).

Process for Preparing a Coated Hard Shell Capsule

Described is a process for preparing a polymer-coated hard shell capsule, suitable as container for pharmaceutical or nutraceutical biologically active ingredients, wherein the hard shell capsule is comprising a body and a cap, wherein in the closed state the cap overlaps the body either in a pre-locked state or in a final-locked state, wherein the hard shell capsule is provided in the pre-locked state and spray-coated with a coating solution, suspension or dispersion comprising a polymer or a mixture of polymers to create a coating layer which covers the outer surface of the hard shell capsule in the pre-locked state.

In a further process step the pre-locked thard shell capsule may be provided with a fill comprising a pharmaceutical or a nutraceutical biologically active ingredient and is closed to the final-locked state.

In such a further process step the polymer-coated hard shell capsule in the pre-locked state may be opened, filled with a fill comprising a pharmaceutical or a nutraceutical biologically active ingredient, and is closed in the final-locked state. This further process step is preferably performed in that the coated hard shell capsule in the pre-locked state is provided to a capsule-filling machine, which performs the opening, filling with a fill comprising a pharmaceutical or a nutraceutical biologically active ingredient and closing of the polymer-coated hard shell capsule to the final-locked state.

This further process step results in a final-locked polymer-coated hard shell capsule, which is a container for pharmaceutical or nutraceutical biologically active ingredient. The final-locked polymer-coated hard shell capsule, which as a container for pharmaceutical or nutraceutical biologically active ingredient is a pharmaceutical or nutraceutical dosage form.

The pharmaceutical or nutraceutical dosage form is comprising a polymer-coated hard shell capsule in the final-locked stage containing a fill comprising a pharmaceutical or nutraceutical biologically active ingredient, wherein the polymer-coated hard shell capsule comprises a coating layer comprising a polymer or a mixture of polymers, where the coating layer covers the outer surface area of the capsule in the pre-locked stage but not the overlapping area where the cap covers the body in the pre-locked stage.

A coating solution comprising the polymer or polymer mixture and optional excipients may be the solution of the polymer in an organic solvent, for instance acetone, isopropanol or ethanol. The concentration of dry weight material in the organic solvent may be about from 5 to 50% by weight of polymer. A suitable spraying concentration may be about 5 to 25% by dry weight.

A coating dispersion may be the dispersion of the polymer or polymer mixture and optional excipients in an aqueous medium, for instance water or a mixture of 80% by weight or more of water and 20% or less by weight of water-soluble solvents, such as acetone or isopropanol. A suitable concentration of dry weight material in the aqueous medium may be from about 5 to 50% by weigh. A suitable spraying concentration may be about 5 to 25% by dry weight.

The spray coating is preferably performed by spraying the coating solution or dispersion onto the pre-locked capsules in a drum coater or in a fluidized bed coating equipment.

Process for Preparing a Fill for the Dosage Form

Suitable processes for preparing the fill for the pharmaceutical or nutraceutical dosage form are well known to a skilled person. A suitable process for preparing the fill for the pharmaceutical or nutraceutical dosage form as disclosed herein may be by forming a core comprising the biologically active ingredient in the form of pellets by direct compression, compression of dry, wet or sintered granules, by extrusion and subsequent rounding off, by wet or dry granulation, by direct pelleting or by binding powders onto active ingredient-free beads or neutral cores or active ingredient-containing particles or pellets and optionally by applying coating layers in the form of aqueous dispersions or organic solutions in spray processes or by fluidized bed spray granulation.

Use/Method of Use/Method Steps

The process for preparing a polymer-coated hard shell capsule suitable as described herein may be understood as a method of use of a hard shell capsule comprising a body and a cap, wherein in the closed stage the cap overlaps the body either in a pre-locked state or in a final-locked state, for preparing a polymer-coated hard shell capsule, suitable as container for pharmaceutical or nutraceutical biologically active ingredients, comprising the steps of
a) providing the hard shell capsule is provided in the pre-locked state and
b) spray-coating with a coating solution, suspension or dispersion comprising a polymer or a mixture of polymers to create a coating layer which covers the outer surface of the hard shell capsule in the pre-locked state.

The spray-coating may be preferably applied by using a drum coater equipment or a fluidized bed coating equipment. A suitable product temperature during the spray-coating process may be in the range from about 15 to 40, preferably from about 20 to 35° C. A suitable spray rate may be in the range from about 0.3 to 4.0, preferably 0.5 to 3.9 [g/min/kg]. After spray-coating a drying step is included.

The polymer-coated hard shell capsule in the pre-locked state may be opened in a step c), filled with a fill comprising a pharmaceutical or a nutraceutical biologically active ingredient in a step d), and is then closed in a step e) to the final-locked state.

Steps c) to e) may be performed manually or preferably supported by a suitable equipment, for instance a capsule-filling machine. Preferably, the coated hard shell capsule in the pre-locked state is provided to a capsule-filling machine, which performs the opening step c), the filling with a fill comprising a pharmaceutical or a nutraceutical biologically active ingredient in step d) and the closing of the capsule to the final-locked state in step e).

The selection of the processes in all their generic or specific features and embodiments as disclosed herein can be combined without restriction with any other generic or specific selections of materials or numerical features and embodiments as disclosed herein, such as polymers, capsule materials, capsule sizes, coating thicknesses, biologically active ingredients and any other embodiments as disclosed.

Pharmaceutical or Nutraceutical Dosage Form

Disclosed is a pharmaceutical or nutraceutical dosage form comprising a polymer-coated hard shell capsule in the final-locked stage containing a fill comprising a pharmaceutical or nutraceutical biologically active ingredient, wherein the polymer-coated hard shell capsule comprises a coating layer comprising a polymer or a mixture of polymers, where the coating layer covers the outer surface area of the capsule in the pre-locked stage. Since the outer surface area of the capsule in the pre-locked stage is larger than outer surface area of the capsule in the final-locked stage a part of the polymer coating layer is hidden or enclosed between the body and the cap of the hard shell capsule, which provides an efficient sealing.

Items

The invention is concerned with following items. The disclosure shall be understood by a skilled person in a broad sense as including any possible combination of any single item or with any other item or other items without limits.

Item 1: Process for preparing a polymer-coated hard shell capsule, suitable as container for pharmaceutical or nutraceutical biologically active ingredients, wherein the hard shell capsule is comprising a body and a cap, wherein in the closed state the cap overlaps the body either in a pre-locked state or in a final-locked state, wherein the hard shell capsule is provided in the pre-locked state and spray-coated with a coating solution, suspension or dispersion comprising a polymer or a mixture of polymers to create a coating layer which covers the outer surface of the hard shell capsule in the pre-locked state.

2. Process according to item 1, wherein the polymer-coated hard shell capsule in the pre-locked state is opened, filled with a fill comprising a pharmaceutical or a nutraceutical biologically active ingredient, and is closed to the final-locked state.

3. Process according to one or more of items 1 or 2, wherein the coated hard shell capsule in the pre-locked state is provided to a capsule-filling machine, which performs opening, filling with a fill comprising a pharmaceutical or a nutraceutical biologically active ingredient and closing of the polymer-coated hard shell capsule to the final-locked state.

4. Process according to one or more of items 1 to 3, wherein the material of the body and the cap is selected from hydroxypropyl methyl cellulose, starch, gelatin, pullulan and a copolymer of C1- to C4-alkylester of (meth)acrylic acid and (meth)acrylic acid.

5. Process according to one or more of items 1 to 4, wherein the polymer or mixture of polymers comprised in the coating layer is selected from the groups of anionic polymers, cationic polymers or neutral polymers.

6. Process according to one or more of items 1 to 5, wherein the polymer or mixture of polymers comprised in the coating layer is an anionic polymer selected from the groups of (meth)acrylate copolymers and celluloses.

7. Process according to one or more of items 1 to 6, wherein the anionic polymer comprised in the coating layer is a copolymer polymerized from 25 to 95, preferably 40 to 95, in particular 60 to 40, % by weight free-radical polymerized C1- to C12-alkyl esters, preferred C1- to C4-alkyl esters of acrylic or of methacrylic acid and 75 to 5, preferably 60 to 5, in particular 40 to 60% by weight from (meth)acrylate monomers with an anionic group.

8. Process according to one or more of items 1 to 7, wherein the polymer or polymer mixture comprised in the coating layer comprises a cationic (meth)acrylate copolymer.

9. Process according to one or more of items 1 to 8, wherein the cationic (meth)acrylate copolymer is polymerized from monomers comprising C1- to C4-alkyl esters of acrylic or of methacrylic acid and an alkyl ester of acrylic or of methacrylic acid with a tertiary or a quaternary ammonium group in the alkyl group.

10. Process according to one or more of items 1 to 8, wherein the polymer or polymer mixture comprised in the coating layer is selected from starch, alginates or salts of alginates, sodium alginate, pectin, shellac, zein, carboxymethyl-zein, modified starch, marine sponge collagen, chitosan, gellan gum, ethyl cellulose and pectin, modified starch and alginate and/or pectin, shellac and alginate and/or pectin, shellac and inulin, whey protein and gums, zein and polyethylene glycol, sodium alginate and chitosan.

11 Process according to one or more of items 1 to 10, wherein the body and the cap are comprising encircling notches and/or dimples in the area, where the cap overlaps the body, that allow the capsule to be closed by a snap-into-place mechanism either in the pre-locked state or in the final-locked state.

12. Process according to one or more of items 1 to 11, wherein the body comprises a tapered rim.

13. Process according to one or more of items 1 to 12, wherein the coating layer is applied in an amount of about 0.7 to 20, 1.0-18, 2 to 10, 4 to 8, 1.0 to 8, 1.5 to 5.5, 1.5 to 4 mg/cm$^2$.

14. Process according to one or more of items 1 to 13, wherein the polymer comprised in the coating layer is a Core-Shell polymer, which is a copolymer from a two stage emulsion polymerization process with a core with 70 to 80% by weight, comprising polymerized units of 65 to 75% by weight of ethyl acrylate and 25 to 35% by weight of methyl methacrylate, and a shell with 20 to 30% by weight, comprising polymerized units of 45 to 55% by weight ethyl acrylate and 45 to 55% by weight methacrylic acid.

15. Polymer-coated hard shell capsule, obtained from a process according to one or more of items 1 to 14.

16. Pharmaceutical or nutraceutical dosage form according to item 16, comprising a polymer-coated hard shell capsule in the final-locked stage containing a fill comprising a pharmaceutical or nutraceutical biologically active ingredient, wherein the polymer-coated hard shell capsule comprises a coating layer comprising a polymer or a mixture of polymers, where the coating layer covers the outer surface area of the capsule in the pre-locked stage.

17. Pharmaceutical or nutraceutical dosage form according to item 16, wherein after 120 min in 0.1 HCl pH 1.2 and subsequent change to a buffered medium (according to USP, for instance USP 40) of pH 6.8 or pH 7.4 about 80% or more of the comprised a pharmaceutical or nutraceutical biologically active ingredient is released after a total time of 165 min (120+45 min). The dissolution test is performed according to the United States Pharmacopeia (USP 40) chapter <711> utilizing USP Apparatus II with a paddle speed of 75 rpm. The test media temperature will be adjusted to 37 +/−0.5° C. Samples will be taken at appropriate time points.

18. Pharmaceutical or nutraceutical dosage form according to item 16 or 17, wherein after 120 min in 0.1 HCl pH 1.2 and 60 min at a subsequent intermediate change to a buffered medium of pH 6.5 or 6.8 and subsequent final change to a buffered medium of pH 7.2 or pH 7.4 about 80% or more of the comprised biologically active ingredient is released after a total time of 225 min or 240 min. The dissolution test is performed according to the United States Pharmacopeia (USP 40) chapter <711> utilizing USP Apparatus II with a paddle speed of 75 rpm. The test media temperature will be adjusted to 37+/−0.5° C. Samples will be taken at appropriate time points.

EXAMPLES

Polymers used in the examples:
EUDRAGIT® FS is a copolymer polymerized from 25% by weight methyl methacrylate, 65% by weight methyl acrylate and 10% by weight methacrylic acid. EUDRAGIT® FS 30 D is an aqueous dispersion comprising 30% by weight EUDRAGIT® FS.

EUDRAGIT® L 100-55 is a copolymer polymerized from 50% by weight ethyl acrylate and 50% by weight methacrylic acid. EUDRAGIT® L 30 D-55 is an aqueous dispersion comprising 30% by weight EUDRAGIT® L 100-55.

EUDRAGIT® NE is a copolymer comprising free-radically polymerized units of 30% by weight of methyl methacrylate and 70% by weight of ethyl acrylate. EUDRAGIT® NE 30 D is an aqueous dispersion comprising 30% by weight EUDRAGIT® NE.

EUDRAGIT® E PO is a copolymer in powder form polymerized from 25% by weight of methyl methacrylate, 25% by weight of butyl methacrylate and 50% by weight of dimethylaminoethyl methacrylate.

Example 1

Dimensions and tolerances of different commercially available capsules with respect to mean difference between pre-locked and locked lengths.

substrate. For this reason coating quantities are expressed as mg of total dry substance per cm² of substrate surface area. Below the equation of pre-locked capsule surface are is described considering the mean difference between the pre-locked state and the accumulated length of the separate capsule halves, body and cap.

TABLE 1

Hard Shell Capsule Dimensions (1/2)

| | Manufacturer | | | | | | | | |
|---|---|---|---|---|---|---|---|---|---|
| | Capsugel | | | Capsugel | | | Capsugel | | |
| | Color | | | | | | | | |
| | Transparent | | | White | | | Transparent | | |
| | Size | | | | | | | | |
| | #0 Vcaps ® plus | | | #0 Vcaps ® plus | | | #1 Vcaps ® plus | | |
| | Locking stage | | | | | | | | |
| | Un-locked | pre-locked | Final-Locked | Un-locked | pre-locked | Final Locked | Un-locked | pre-locked | Final Locked |
| Length [mm] | 29.16 | 23.65 | 21.38 | 29.16 | 23.76 | 20.91 | 26.39 | 21.19 | 19.03 |
| SD [mm] | | 0.19 | 0.2 | | 0.16 | 0.17 | | 0.15 | 0.07 |
| Minimum [mm] | | 23.25 | 21 | | 23.43 | 20.67 | | 20.95 | 18.9 |
| Maximum [mm] | | 23.95 | 21.7 | | 23.99 | 21.31 | | 21.4 | 19.15 |
| Overlap length [mm] | | 5.51 | 2.27 | | 5.4 | 2.85 | | 5.2 | 2.16 |
| Total Overlap length [mm] | | 7.78 | | | 8.25 | | | 7.36 | |
| Overlap level | | 71% | 100% | | 65% | 100% | | 71% | 100% |

TABLE 2

Hard Shell Capsule Dimensions (2/2)

| | Manufacturer | | | | | | | | |
|---|---|---|---|---|---|---|---|---|---|
| | Capsugel | | | ACG | | | ACG | | |
| | Color | | | | | | | | |
| | Transparent | | | Transparent | | | White | | |
| | Size | | | | | | | | |
| | #3 Vcaps ® plus | | | #0 Naturecaps | | | #0EL Naturecaps | | |
| | Locking stage | | | | | | | | |
| | Un-locked | pre-locked | Final Locked | Un-locked | pre-locked | Final Locked | Un-locked | pre-locked | Final Locked |
| Length [mm] | 21.67 | 17.69 | 15.74 | 29.2 | 23.04 | 20.92 | 32 | 25.17 | 22.87 |
| SD [mm] | | 0.16 | 0.17 | | 0.12 | 0.16 | | 0.07 | 0.17 |
| Minimum [mm] | | 17.39 | 15.23 | | 22.65 | 20.68 | | 25.01 | 22.59 |
| Maximum [mm] | | 17.94 | 15.98 | | 23.21 | 21.22 | | 25.29 | 23.1 |
| Overlap length [mm] | | 3.98 | 1.95 | | 6.16 | 2.12 | | 6.83 | 2.3 |
| Total Overlap [mm] | | 5.93 | | | 8.28 | | | 9.13 | |
| Overlap level | | 67% | 100% | | 74% | 100% | | 75% | 100% |

Example 2—Surface Area Calculation and Colon Targeting Coating of Pre-Locked Capsules in Drum Coater Since a certain coating layer thickness is required to achieve the desired film functionality, the required amount of coating material depends on the surface area of the $$A_{\frac{1}{2}Sphere} = 2\left(\frac{d}{2}\right)^2 \pi$$

$$A_{Cylinder,body} = 2\pi\left(\frac{d}{2}\right)(h - h_{overlap})$$

-continued $$A_{Cylinder, cap} = 2\pi\left(\frac{d}{2}\right)h$$

$$A_{Capsule-segment} = A_{\frac{1}{2}Sphere} + A_{Cylinder}$$

$$A_{Pre-locked\ capsule} = A_{Body} + A_{Cylinder}$$

Calculation of a coating formulation for a functional enteric coating of pre-locked capsules.

Polymer dry substance [g] = polymer weight $$\text{gain}\left[\frac{mg}{100*cm^2}\right]A_{Pre-locked\ capsule}[mm^2]\left(\frac{\text{Batch size [g]}}{W_{Pre-locked\ capsule}[mg]}\right)$$

Furthermore, a coating formulation may include in addition to the polymer further suitable excipients like plasticizer, anti-tacking agent, etc. In order to calculate suitable excipient amounts [E], the amount of each respective excipient based on dry polymer substance in % needs to be calculated. In order to calculate the total weight gain, the polymer weight gain has to be multiplied with the factor [E].

$$E = \frac{100\% + E_1 + E_2 + \ldots + E_n}{100\%}$$

Total dry substance [g] = polymer weight gain$\left[\frac{mg}{100*cm^2}\right]$ $$A_{Pre-locked\ capsule}[mm^2]\left(\frac{\text{Batch size [g]}}{W_{Pre-locked\ capsule}[mg]}\right)E$$

Figure 1:
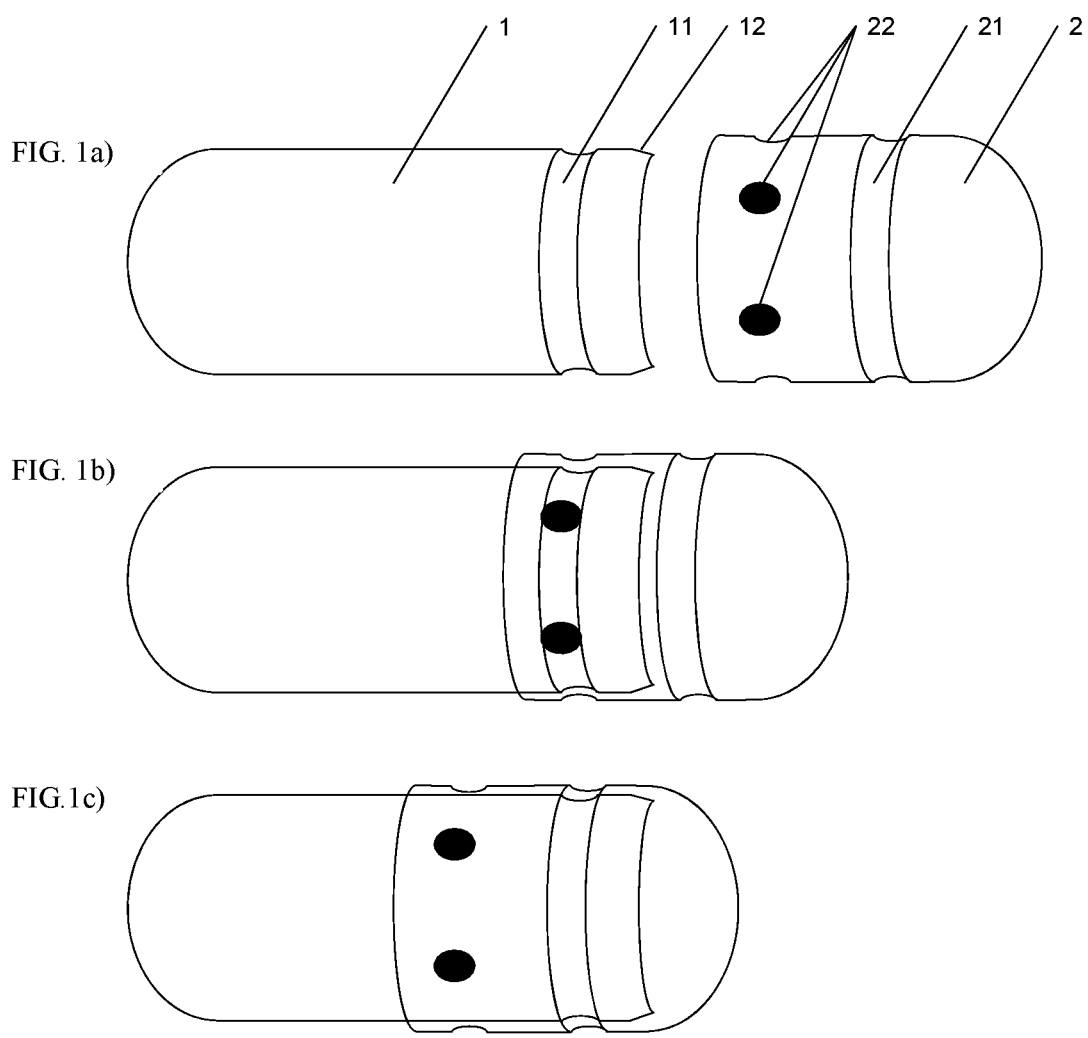
FIG. 1 includes FIGS. 1a, 1b and 1c.
Figure 2:
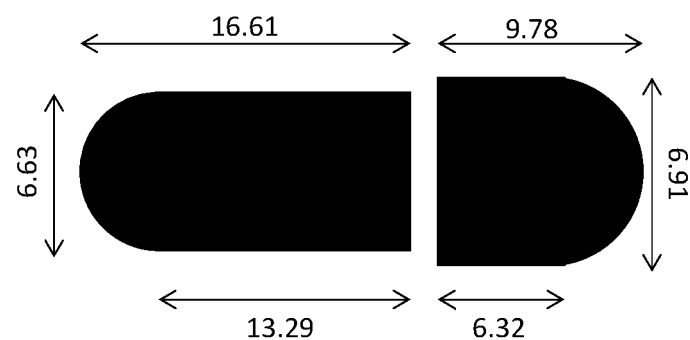
FIG. 2 shows a schematic drawing of the body (left) and the cap (right) of a Vcaps® Plus size #1 hard shell capsule with the relevant dimensions in mm. The dimensions are used in example 2 for the calculation of the outer capsule surface in the pre-locked state.

Calculation Example 2 for the Calculation of the Outer Capsule Surface in the Pre-Locked State FIG. 2 shows a schematic drawing of the body (left) and the cap (right) of a Vcaps® Plus size 1 hard shell capsule with the relevant dimensions in mm. The dimensions are used in the calculation example 2 for the calculation of the outer capsule surface in the pre-locked state. The dimensions are:

Body: length=16.61 mm, cylinder (length of the cylindrical part)=13.29 mm, outer diameter=6.63 mm Cap: length=9.78 mm, cylinder (length of the cylindrical part)=6.32 mm, outer diameter=6.91 mm $$A_{\frac{1}{2}Sphere,\ Body} = 2\left(\frac{6.63}{2}\right)^2\pi = 69.05\ [mm^2]$$

$$A_{Cylinder,\ Body} = 2\pi\left(\frac{6.63}{2}\right)(13.29 - 5.2) = 168.50\ [mm^2]$$

$$A_{\frac{1}{2}Sphere,\ Cap} = 2\left(\frac{6.91}{2}\right)^2\pi = 75.00\ [mm^2]$$

$$A_{Cylinder,\ Cap} = 2\pi\left(\frac{6.91}{2}\right)6.32 = 137.20\ [mm^2]$$

$$A_{Capsule-body} = 69.05 + 168.50 = 237.55\ [mm^2]$$

$$A_{Capsule-cap} = 75.00 + 137.20 = 212.20\ [mm^2]$$

$$A_{Pre-locked\ capsule} = 237.55 + 212.20 = 449.75\ [mm^2]$$

TABLE 4

| Capsuls Surface Area | | |
|---|---|---|
| Parameter | Body | Cap |
| $A_{1/2\ Sphere}$ [mm²] | 69.05 | 75.00 |
| $A_{Cylinder}$ [mm²] | 168.50 | 137.20 |
| $A_{Segment}$ [mm²] | 237.55 | 212.20 |
| $A_{Pre-locked\ capsule}$ [mm²] | 449.75 | |

TABLE 3

| Vcaps ® Plus Capsule Specifications: | | | | | | | | | |
|---|---|---|---|---|---|---|---|---|---|
| Size | 00el | 00 | 0el | 0 | 1 | 1el | 2 | 3 | 4 |
| Weight | | | | | | | | | |
| Weight [mg] | 130 | 122 | 107 | 96 | 76 | 81 | 61 | 47 | 38 |
| Tolerance [mg] | ±10 | ±7 | ±7 | ±6 | ±5 | ±5 | ±4 | ±3 | ±3 |
| Length of the capsules halves (body and cap) | | | | | | | | | |
| Body [mm] | 22.20 | 20.22 | 20.19 | 18.44 | 16.61 | 17.70 | 15.27 | 13.59 | 12.19 |
| Tolerance [mm] | ±0.46 | ±0.46 | ±0.46 | ±0.46 | ±0.46 | ±0.46 | ±0.46 | ±0.46 | ±0.46 |
| Cap [mm] | 12.95 | 11.74 | 11.68 | 10.72 | 9.78 | 10.49 | 8.94 | 8.08 | 7.21 |
| Tolerance [mm] | ±0.46 | ±0.46 | ±0.46 | ±0.46 | ±0.46 | ±0.46 | ±0.46 | ±0.46 | ±0.46 |
| External diameter | | | | | | | | | |
| Body [mm] | 8.18 | 8.18 | 7.34 | 7.34 | 6.63 | 6.63 | 6.07 | 5.57 | 5.05 |
| Cap [mm] | 8.53 | 8.53 | 7.65 | 7.64 | 6.91 | 6.91 | 6.35 | 5.82 | 5.32 |
| Overall length in the final-locked state | | | | | | | | | |
| Length [mm] | 25.3 | 23.30 | 23.5 | 21.70 | 19.40 | 20.40 | 18.00 | 15.90 | 14.30 |
| Tolerance [mm] | ±0.30 | ±0.30 | ±0.30 | ±0.30 | ±0.30 | ±0.30 | ±0.30 | ±0.30 | ±0.30 |

Amount polymer dry polymer substance:

Dry polymer substance [g] =

$$5\left[\frac{mg}{100*cm^2}\right]449.75[mm^2]\left(\frac{300[g]}{76[mg]}\right) = 88.77[g]$$

Amount Total Dry Substance:

$$E = \frac{100\% + 17\% + 10\% + 2.5\%}{100\%} = 1.295$$

Total dry substance [g] =

$$5\left[\frac{mg}{100*cm^2}\right]449.75[mm^2]\left(\frac{300[g]}{76[mg]}\right)1.295 = 114.96[g]$$

Formulation Example 2 for Colon Targeting with Vcaps® Plus Size 1

EUDRAGIT® FS 30 D and EUDRAGIT® L 30 D-55 are aqueous polymer dispersions with each 30% by weight polymer content. The polymer dispersions EUDRAGIT® FS 30 D and EUDRAGIT® L 30 D-55 were mixed in a container. The excipients were added into the water while gently stirring. The excipient suspension was added to the polymer dispersion mixture. The spraying suspension was gently stirred during the coating process.

Vcaps® plus size 1 capsules were coated in the pre-locked state utilizing a drum coater. Afterwards, capsules were manually filled with 200 mg Caffeine and closed to the final-locked state.

TABLE 5

Formulation Example 2 - Vcaps ® Plus Size 1 (batch size 300 g)

| Material | Composition | Amounts | Dry substance | Solid Composition Percentage |
|---|---|---|---|---|
| EUDRAGIT® FS 30 D | 4.0 mg/cm² | 295.89 g | 88.77 g | 77.21% |
| EUDRAGIT® L 30 D-55 | 1.0 mg/cm² | | | |
| Glyceryl Monostearate (40-55%) | 8.5% on ds* | 7.55 g | 7.55 g | 6.57% |
| Plosysorbat 80 (33% aq) | 10.3% on ds* | 27.81 g | 9.18 g | 7.99% |

TABLE 5-continued

Formulation Example 2 - Vcaps ® Plus Size 1 (batch size 300 g)

| Material | Composition | Amounts | Dry substance | Solid Composition Percentage |
|---|---|---|---|---|
| Triethyl citrate | 10.7% on ds* | 9.46 g | 9.46 g | 8.23% |
| Demineralized Water | On demand | 425.34 g | n/a | n/a |
| Total | n/a | 766.35 g | 114.95 g | |
| Solid content | 15% w/w | | | |
| Total solid weight gain | 6.5 mg/cm² | | | |

*Quantity based on dry polymer substance [%]

TABLE 6

Process Parameter Example 2

| Parameter | Value |
|---|---|
| Machine | Lödige LHC |
| Nozzle bore [mm] | 1.0 |
| Internal tube diameter [mm] | 1.0 |
| Delivery system | Verder Lab Peristaltic Pump |
| Atomizing pressure [bar] | 0.4 |
| Flat pattern pressure [bar] | 0.4 |
| Pan speed [rpm] | 20-22 |
| Inlet air volume [m³/h] | 90-92 |
| Inlet air temperature [° C.] | 29-39 |
| Exhaust air temperature [° C.] | 26-30 |
| Product temperature [° C.] | 26-30 |
| Spray rate [g/min/kg] | 0.8-2.7 |
| Exhaut air humidity [% r.h.] | 30.0-37.5 |

LOD

| Capsule | prior coating | 4.1% |
| Capsule | intermediate sample 2.5 mg/cm² | 4.7% |
| Capsule | final sample 5 mg/cm² | 4.6% |

Dissolution Test Method:
Apparatus: ERWEKA DT 700 Paddle Apparatus (USP II)
Detection method: Online UV
Temperature: 37.5° C.
Media I: 700 ml 0.1 N HCL adjusted to pH 1.20 (by using 2 N NaOH and 2 N HCl)
Media II: After 2 hours in media 1194 ml 0.2 N Na$_3$PO$_4$ solution added to increase pH to 6.5 (fine adjustment of pH by using 2 N NaOH and 2 N HCl)
Media III: After an additional hour in media II 67 ml 0.2 N Na$_3$PO$_4$ solution added to increase pH to 7.2 (again fine adjustment of pH by using 2 N NaOH and 2 N HCl).
Paddle Speed: 75 rpm

TABLE 7

Dissolution Results Example 2

| Media | Time [min] | Sample 1 6.5 mg/cm² [% released] | Sample 2 6.5 mg/cm² [% released] | Sample 3 6.5 mg/cm² [% released] | Sample 1 5.2 mg/cm² [% released] | Sample 2 5.2 mg/cm² [% released] | Sample 3 5.2 mg/cm² [% released] |
|---|---|---|---|---|---|---|---|
| 0.1N HCl | 0 | 0.00 | 0.00 | 0.00 | 0.00 | 0.00 | 0.00 |
| 0.1N HCl | 60 | 0.00 | 0.00 | 0.00 | 0.00 | 0.00 | 0.00 |
| 0.1N HCl | 120 | 0.00 | 0.00 | 0.00 | 0.00 | 0.00 | 0.00 |
| pH 6.5 | 135 | 0.00 | 0.00 | 0.00 | 0.00 | 0.00 | 0.00 |
| pH 6.5 | 150 | 0.00 | 0.00 | 0.00 | 0.00 | 0.00 | 0.00 |
| pH 6.5 | 165 | 0.41 | 0.11 | 0.13 | 0.00 | 0.00 | 0.00 |

TABLE 7-continued

Dissolution Results Example 2

| Media | Time [min] | Sample 1 6.5 mg/cm$^2$ [% released] | Sample 2 6.5 mg/cm$^2$ [% released] | Sample 3 6.5 mg/cm$^2$ [% released] | Sample 1 5.2 mg/cm$^2$ [% released] | Sample 2 5.2 mg/cm$^2$ [% released] | Sample 3 5.2 mg/cm$^2$ [% released] |
|---|---|---|---|---|---|---|---|
| pH 6.5 | 180 | 1.00 | 0.62 | 0.77 | 0.47 | 0.24 | 0.11 |
| pH 7.4 | 185 | 1.47 | 1.10 | 1.37 | 0.87 | 0.49 | 0.32 |
| pH 7.4 | 190 | 2.05 | 2.87 | 2.11 | 3.16 | 0.92 | 1.03 |
| pH 7.4 | 195 | 17.67 | 7.70 | 2.98 | 19.66 | 24.48 | 22.23 |
| pH 7.4 | 210 | 92.26 | 45.15 | 63.04 | 96.67 | 99.78 | 90.81 |
| pH 7.4 | 225 | 99.92 | 99.79 | 99.93 | 99.88 | 99.88 | 99.83 |
| pH 7.4 | 240 | 99.88 | 99.86 | 99.86 | 99.93 | 99.92 | 99.92 |
| pH 7.4 | 255 | 99.95 | 99.92 | 99.91 | 99.95 | 99.94 | 99.92 |
| pH 7.4 | 270 | 99.96 | 99.94 | 99.93 | 99.96 | 99.96 | 99.92 |
| pH 7.4 | 300 | 100.01 | 100.00 | 99.97 | 99.99 | 99.97 | 99.97 |

Another example utilizing a polymer blend for colon targeting. The results nicely show a successful in-vitro evaluation with resistance in the stomach (pH 1.2) and upper small intestine (pH 6.5) and release at ileocecal valve/colonic pH 7.4. The coating process was well established avoiding significant water uptake of the capsule shell.

Example 3—Enteric Coating of Pre-Locked Capsules in Drum Coater

EUDRAGIT® L 30 D-55 was provided as 30% by weight aqueous polymer dispersion. The Additional excipients were added into the water while gently stirring. The excipient suspension was added to the polymer dispersion. The spraying suspension was gently stirred during the coating process. The capsules were coated in the pre-locked state utilizing a drum coater. Afterwards, capsules were manually filled with 200 mg Caffeine and closed to the final-locked state.

TABLE 8

Formulation Example 3 - Vcaps ® Plus Size 1 (Batch size: 300 g)

| Material | Composition | Solid Composition Percentage |
|---|---|---|
| EUDRAGIT ® L 30 D-55 | 5.5 mg/cm$^2$ | 77.77% |
| Glyceryl Monostearate (40-55%) | 7.5% on ds* | 5.83% |
| Polysorbate ® 80 | 3.0% on ds* | 2.33% |
| Triethyl citrate | 18.1% on ds* | 14.07% |
| Demineralized Water | On demand | n/a |
| Solid content | 16% w/w | |
| Total solid weight gain | 7.1 mg/cm$^2$ | |

*Quantity based on dry polymer substance [%]

TABLE 9

Process Parameter Example 3

| Parameter | Value |
|---|---|
| Machine | Lödige LHC |
| Batch size [g] | 91 |
| Nozzle bore [mm] | 1.2 |
| Internal tube diameter [mm] | 1.0 |
| Peristaltic pump | Verder lab |
| Atomizing pressure [bar] | 0.4 |
| Flat pattern pressure [bar] | 0.4 |
| Room temperature [° C.] | 22.8-24.1 |
| Room humidity [% r.h.] | 36.6-38.7 |
| Pan speed [rpm] | 22 |
| Inlet air volume [m$^3$/h] | 74-76 |
| Inlet air temperature [° C.] | 28.6-33.5 |
| Exhaust air temperature [° C.] | 26.6-29.5 |
| Product temperature [° C.] | 25.8-27.4 |
| Spray rate [g/min/kg] | 0.9-4.6 |
| Exhaut air humidity [% r.h.] | 31.8-38.0 |
| Process time [min] | 68 |

Dissolution Test

The polymer-coated pre-locked capsules were manually filled with 200 mg Caffeine, closed to the final-locked state and tested in a dissolution test.

Method:
Apparatus: ERWEKA DT 700 Paddle Apparatus (USP II)
Detection method: Online UV
Temperature: 37.5° C.
Media I: 700 ml 0.1 N HCL adjusted to pH 1.2 (by using 2 N NaOH and 2 N HCl)
Media II: After 2 hours in media 1214 ml 0.2 N Na$_3$PO$_4$ solution added to increase pH to 6.8 (fine adjustment of pH by using 2 N NaOH and 2 N HCl)
Paddle speed: 75 rpm

TABLE 10

Dissolution Results- Example 3

| Media | Time [min] | Sample 1 7.1 mg/cm$^2$ [% released] | Sample 2 7.1 mg/cm$^2$ [% released] | Sample 3 7.1 mg/cm$^2$ [% released] | Sample 1 5.1 mg/cm$^2$ [% released] | Sample 2 5.1 mg/cm$^2$ [% released] | Sample 3 5.1 mg/cm$^2$ [% released] |
|---|---|---|---|---|---|---|---|
| 0.1N HCL | 0 | 0.00 | 0.00 | 0.00 | 0.00 | 0.00 | 0.00 |
| 0.1N HCL | 30 | 0.00 | 0.00 | 0.00 | 0.00 | 0.00 | 0.00 |
| 0.1N HCL | 60 | 0.00 | 0.00 | 0.00 | 0.00 | 0.00 | 0.00 |
| 0.1N HCL | 90 | 0.00 | 0.00 | 0.00 | 0.00 | 0.00 | 0.00 |
| 0.1N HCL | 120 | 0.00 | 0.00 | 0.00 | 0.00 | 0.00 | 0.00 |
| pH 6.8 | 130 | 0.28 | 0.13 | 0.08 | 0.18 | 0.10 | −0.03 |
| pH 6.8 | 140 | 73.21 | 43.84 | 45.92 | 54.60 | 50.76 | 64.65 |
| pH 6.8 | 150 | 99.83 | 87.28 | 97.74 | 92.97 | 85.50 | 95.25 |
| pH 6.8 | 165 | 100.07 | 99.87 | 100.36 | 99.46 | 99.70 | 99.93 |

TABLE 10-continued

Dissolution Results- Example 3

| Media | Time [min] | Sample 1 7.1 mg/cm² [% released] | Sample 2 7.1 mg/cm² [% released] | Sample 3 7.1 mg/cm² [% released] | Sample 1 5.1 mg/cm² [% released] | Sample 2 5.1 mg/cm² [% released] | Sample 3 5.1 mg/cm² [% released] |
|---|---|---|---|---|---|---|---|
| pH 6.8 | 180 | 100.07 | 99.99 | 100.07 | 99.79 | 100.32 | 99.86 |
| pH 6.8 | 210 | 100.14 | 99.93 | 100.26 | 99.81 | 100.18 | 99.98 |
| pH 6.8 | 240 | 100.10 | 99.98 | 100.37 | 99.83 | 100.48 | 100.35 |

Example C4 (Comparative Example)—Fluidized Bed Coating of Separated Capsule Halves (Body and Cap)

EUDRAGIT® FS 30 D was provided as 30% by weight aqueous polymer dispersion. The excipients were added into the water while gently stirring. The excipient suspension was added to the polymer dispersion. The spraying suspension was gently stirred during the coating process.

The capsules were coated in the pre-locked state utilizing a fluidized bed coater. Afterwards, capsules were manually filled with 200 mg Caffeine.

TABLE 11

Formulation Example C4 - Vcaps ® Plus Size 0

| Material | Composition | Composition | Solid composition Percentage |
|---|---|---|---|
| Capsule Segment | bodies | caps | |
| Batch size (Capsule start weight) | 36 g | 35 g | |
| EUDRAGIT ® FS 30 D | 6.0 mg/cm² | 6.0 mg/cm² | 83.67% |
| Glyceryl Monostearate (40-55%) | 8.5% on ds* | 8.5% on ds* | 7.11% |
| Polysorbate ® 80 | 0.34% on ds* | 0.34% on ds* | 0.28% |
| Triethyl citrate | 10.66% on ds* | 10.66% on ds* | 8.92% |
| Demineralized Water | On demand | On demand | n/a |
| Solid content | 10% w/w² | 10% w/w² | |
| Total solid weight gain | 7.2 mg/cm² | 7.2 mg/cm² | |

*Quantity based on dry polymer substance [%]

TABLE 12

Process Parameter Example C4

| Parameter | Value | Value |
|---|---|---|
| Machine | Bosch Hüttlin Mycrolab with small product container | |
| Batch size [g] | 36 | 35 |
| Nozzle bore [mm] | 0.8 | 0.8 |
| Internal tube diameter [mm] | 1.0 | 1.0 |
| Peristaltic pump | Flocon periflo 1003 | |
| Atomizing pressure [bar] | 1.0 | 1.0 |
| Micro climate [bar] | 0.2-0.4 | 0.2 |
| Room temperature [° C.] | 23.4-23.6 | 22.4-22.9 |
| Room humidity [% r.h.] | 35.1-38.5 | 35.5-37.0 |
| Inlet air volume [m³/h] | 19.9-23.0 | 19.0-22.0 |
| Inlet air temperature [° C.] | 25.0-27.1 | 24.9-28.0 |
| Exhaust air temperature [° C.] | 19.4-21.5 | 18.9-21.5 |
| Product temperature [° C.] | 22.5-25.2 | 21.0-23.6 |
| Spray rate [g/min] | 1.6-2.8 | 1.6-2.6 |
| Exhaust air humidity [% r.h.] | 33.1-46.9 | 34.4-48.2 |
| Process time [min] | 99 | 73 |

Investigation of Capsule Roundness of Bodies and Caps

Equipment:
Light optical microscope ZEISS AXIO Zoom.V16
Objektive ZEISS PlanNeoFluar Z 1×/0.25 FWD 56 mm
Light source SCHOTT MC 1500
Incident light-ring light SCHOTT S80-55
Camera ZEISS Axiocam 503 color
Software AxioVision SE64
Software for image analysis Oympus Soft Imaging Solutions GmbH Sample Preparation:

The capsule halves, cap and body, were separately analyzed. For each investigation n=10 samples per half were investigated. Therefore, the capsule halves were put into a sample holder with the open end in vertical up direction. Afterwards, the samples were analyzed with above listed equipment.

Sample Investigation:

The microscope was set up with a 10-fold magnification, the focal area wans the capsule shell as observed from the vertical down direction. The capsules position was adjusted to avoid and shadow related to a non-vertical position. As relevant focal area, light intensity and contrast needs to be properly adjusted.

Imaging and Table of Results:

The images were recorded as black and white images (capsule bodies FIG. 3 and caps FIG. 4) and transferred into the scandium database. The capsule shell circumference as investigated from the vertical down position was selected utilizing the software toolbox. For that circumference the area [mm²], feret diameter and circumference length was detected and calculated. The feret diameter or feret's diameter is a measure of an object size along a specified direction. In general, it can be defined as the distance between the two parallel planes restricting the object perpendicular to that direction. It is therefore also called the caliper diameter, referring to the measurement of the object size with a caliper. The results are reported in the table below outlining minimum, maximum, average and standard deviation for the circumference area [mm²], feret diameter and length. The measurement was repeated for each capsule cap and body sample in total 20 times. The utilized shape factor is the aspect ratio, a function of the largest diameter and the smallest diameter orthogonal to it:

$$\text{Aspect Ratio} = \frac{d_{min}}{d_{max}}$$

The normalized aspect ratio varies from about 1 for an uncoated capsule without deformation and increasing values depending on the degree of deformation.

TABLE 13

Capsule Roundness Results

| | BODY | | | | | CAP | | | |
|---|---|---|---|---|---|---|---|---|---|
| Image no. [2D Object] | Area [mm²] | Feret Average [mm] | Length [mm] | Aspect Ratio | Image no. [2D Object] | Area [mm²] | Feret Average [mm] | Length [mm] | Aspect Ratio |
| B1 | 39.1 | 7.39 | 26.33 | 1.51 | C1 | 44.7 | 7.69 | 26.77 | 1.28 |
| B2 | 40.6 | 7.37 | 28.31 | 1.17 | C2 | 42.6 | 7.61 | 28.63 | 1.42 |
| B3 | 41.7 | 7.43 | 25.06 | 1.15 | C3 | 45.2 | 7.69 | 30.36 | 1.20 |
| B4 | 42.3 | 7.43 | 24.77 | 1.22 | C4 | 44.7 | 7.64 | 28.76 | 1.20 |
| B5 | 41.6 | 7.34 | 24.51 | 1.09 | C5 | 45.1 | 7.61 | 26.22 | 1.02 |
| B6 | 39.6 | 7.33 | 24.75 | 1.32 | C6 | 43.8 | 7.56 | 28.26 | 1.12 |
| B7 | 38.6 | 7.29 | 24.44 | 1.48 | C7 | 44.5 | 7.64 | 26.33 | 1.22 |
| B8 | 38.9 | 7.33 | 24.57 | 1.45 | C8 | 43.4 | 7.59 | 27.37 | 1.29 |
| B9 | 42.0 | 7.44 | 24.69 | 1.29 | C9 | 44.2 | 7.64 | 27.19 | 1.28 |
| B10 | 41.3 | 7.32 | 24.34 | 1.08 | C10 | 44.1 | 7.60 | 26.53 | 1.25 |
| Min | 38.6 | 7.29 | 24.34 | 1.08 | Min | 42.6 | 7.56 | 26.22 | 1.02 |
| Average | 40.6 | 7.37 | 25.18 | 1.28 | Average | 44.2 | 7.63 | 27.64 | 1.23 |
| Max | 42.3 | 7.44 | 28.31 | 1.51 | Max | 45.2 | 7.69 | 30.36 | 1.42 |

SEM Analysis

SEM investigation of separate coated capsules halves, bodies and caps, have shown that fissures were formed around the tampered rim. Furthermore, it was observed on macroscopic and scanning microscope images that the separately coated caps and body showed significant deformation tendencies during the coating process, which seems not to be reversible. Such deformation lead to difficulties during the manual encapsulation process, which allow the assumption that an automatic encapsulation process is not feasible as only selected caps and bodies fits to each other. Therefore, a fluidized bed coating of separated capsules is not a suitable process to produce capsules with allow automatic capsule filling.

Dissolution Test

Capsule Manually Filled with 200 mg Caffeine

Method:

Apparatus: ERWEKA DT 700 Paddle Apparatus (USP II)

Detection method: Online UV

Temperature: 37.5° C.

Media I: 700 ml 0.1 N HCL adjusted to pH 1.20 (by using 2 N NaOH and 2 N HCl)

Media II: After 2 hours in media 1214 ml 0.2 N $Na_3PO_4$ solution added to increase pH to 6.8 (fine adjustment of pH by using 2 N NaOH and 2 N HCl)

Media III: After an additional hour in media II 46 ml 0.2 N $Na_3PO_4$ solution added to increase pH to 7.4 (again fine adjustment of pH by using 2 N NaOH and 2 N HCl).

Paddle speed: 75 rpm

TABLE 14

Dissolution Results Example C4

| Media | Time [min] | Sample 1 7.2 mg/cm² [% released] | Sample 2 7.2 mg/cm² [% released] | Sample 3 7.2 mg/cm² [% released] | Sample 1 6 mg/cm² [% released] | Sample 2 6 mg/cm² [% released] | Sample 3 6 mg/cm² [% released] |
|---|---|---|---|---|---|---|---|
| 0.1N HCl | 0 | 0.00 | 0.00 | 0.00 | 0.00 | 0.08 | 0.00 |
| 0.1N HCl | 15 | 0.00 | 0.00 | 0.00 | 0.00 | 0.06 | 0.00 |
| 0.1N HCl | 30 | 0.00 | 0.00 | 0.00 | 0.00 | 0.11 | 0.00 |
| 0.1N HCl | 60 | 0.00 | 0.00 | 0.00 | 0.00 | 0.15 | 0.24 |
| 0.1N HCl | 120 | 0.00 | 0.00 | 0.00 | 0.00 | 0.31 | 1.12 |
| pH 6.8 | 135 | 0.00 | 0.00 | 0.00 | 0.00 | 0.34 | 1.96 |
| pH 6.8 | 150 | 0.00 | 0.00 | 0.00 | 0.00 | 0.43 | 2.28 |
| pH 6.8 | 165 | 0.00 | 0.00 | 0.00 | 0.00 | 0.50 | 2.52 |
| pH 6.8 | 180 | 0.00 | 0.00 | 0.00 | 0.00 | 0.46 | 5.50 |
| pH 7.4 | 185 | 0.00 | 0.00 | 0.00 | 0.00 | 0.39 | 6.20 |
| pH 7.4 | 190 | 0.00 | 0.00 | 0.00 | 0.00 | 0.51 | 5.84 |
| pH 7.4 | 195 | 0.00 | 0.00 | 0.00 | 0.00 | 2.14 | 5.95 |
| pH 7.4 | 210 | 77.00 | 0.78 | 79.88 | 75.40 | 99.76 | 100.56 |
| pH 7.4 | 225 | 99.69 | 99.58 | 99.44 | 99.64 | 99.86 | 99.30 |
| pH 7.4 | 240 | 99.76 | 99.86 | 99.92 | 99.85 | 100.13 | 99.16 |
| pH 7.4 | 255 | 99.81 | 99.94 | 100.07 | 99.91 | 100.15 | 99.59 |
| pH 7.4 | 270 | 99.83 | 100.07 | 99.91 | 100.10 | 100.14 | 100.37 |
| pH 7.4 | 285 | 99.94 | 99.95 | 99.93 | 99.93 | 100.12 | 100.27 |
| pH 7.4 | 300 | 99.82 | 99.95 | 99.96 | 99.96 | 100.18 | 101.53 |

The manual encapsulation of the described formulation and process led to a reject rate considering a first time right of the encapsulation of 85%. The dissolution test below was performed with capsules which were filled first time right. First time right means that the capsules were filled and then closed in a first iteration.

Example 5—Enteric Coating Pre-Locked Capsules in Drum Coater and Automatic Capsule Filling In order to calculate the maximum weight gain suitable for an encapsulation process the maximum layer thickness was predicted as equal to the gap width between capsule cap and body of pre-locked or final-locked capsules. In example 11 the average gap width of Vcaps® Plus capsules was calculated with 50 μm. Furthermore, the absolute density of a coating was predicted with approx. 1 mg/cm³, the value was verified by scanning electron microscope investigations of samples.

Layer thickness [μm] =
$$\text{total weight gain} \left[\frac{mg*10000}{cm^2}\right] / \text{absolute density} \left[\frac{g*1000}{cm^3}\right]$$

TABLE 15

Predicted Layer Thickness

| Total weight gain | Predicted layer thickness |
|---|---|
| 2.6 mg/cm² | 26 μm |
| 3.9 mg/cm² | 39 μm |
| 5.1 mg/cm² | 51 μm |

The EUDRAGIT® polymer (s) were mixed in a suitable sized container. The additional excipients were added into the water while gently stirring. After a suitable post stirring time the excipient suspension was added to the polymer dispersion. The spraying suspension was gently stirred during the coating process. The capsules were coated in the pre-locked state utilizing a drum coater.

TABLE 16

Formulation Example 5- Vcaps ® Plus Size 0 (Batch size 300 g)

| Material | Composition | Solid Composition Percentage |
|---|---|---|
| EUDRAGIT ® L 30 D-55 | 4 mg/cm² | 77.77% |
| Glyceryl monostearate (40-55%) | 7.5% on ds* | 5.83% |
| Polysorbate ® 80 | 3.0% on ds* | 2.33% |
| Triethyl citrate | 18.1% on ds* | 14.07% |
| Demineralized water | On demand | n/a |
| Solid content | 16% w/w | |
| Total solid weight gain | 5.1 mg/cm² | |

*Quantity based on dry polymer substance [%]

TABLE 17

Process Parameter Example 5

| Parameter | Value |
|---|---|
| Machine | Lödige LHC |
| Batch size [g] | 300 |
| Nozzle bore [mm] | 1.0 |
| Internal tube diameter [mm] | 1.0 |
| Peristaltic pump | Verder lab |
| Atomizing pressure [bar] | 0.5 |
| Flat pattern pressure [bar] | 0.5 |
| Room temperature [° C.] | 22.6-23.1 |
| Room humidity [% r.h.] | 39.6-47.0 |
| Pan speed [rpm] | 15 |
| Inlet air volume [m³/h] | 90-92 |
| Inlet air temperature [° C.] | 35.0-42.7 |
| Exhaust air temperature [° C.] | 24.7-28.4 |
| Product temperature [° C.] | / |
| Spray rate [g/min/kg] | 3.5-10.5 |
| Exhaut air humidity [% r.h.] | 37.1-53.2 |
| Process time [min] | 81 |

Encapsulation Parameter

A 400 mg of a 50:50 blend with MCC and Caffeine was filled into the polymer-coated pre-locked capsules using an automatic MG2 Labby Capsule filling equipment with a powder filling set up using standard format size 0 tooling for capsule opening, transport, filling and closing. The machine output was set to 2000 cps/hour.

Capsules tested in automatic capsule filling machine, 2.6 and 3.9 mg/cm² total solid weight gain feasible to process automatically. At 5.1 mg/cm² total solid weight gain the limitation was the standard tooling which was not able to operate with the pre-locked capsules due to the increased layer thickness. In order to investigate, if polymer weight gains above 4 mg/cm² for that particular formulation could observed modified tooling would be required considering the increased capsule diameter.

Description of the SEM Analysis of Bodies and Caps

The coating of the pre-locked capsules allows superior capsules filling in comparison to fluid be coated separated capsules. The advantage is that the pre-locked capsules provide more mechanical stability in comparison to separated capsule pieces. Furthermore, coated pre-locked capsules ensure that during the filling process the two capsules pieces will fit to each other. Furthermore, the tampered rim is intact and supports sliding of the caps over the body until the capsule is final-locked. It is proven that the pre-locked coated tablets could be separated in a capsule filling machine also when both pieces are slightly bridged.

Dissolution Test

Method:

Apparatus: ERWEKA DT 700 Paddle Apparatus (USP II)
Detection method: Online UV
Temperature: 37.5° C.
Media I: 700 ml 0.1 N HCL adjusted to pH 1.20 (by using 2 N NaOH and 2 N HCl)
Media II: After 2 hours in media 1214 ml 0.2 N Na₃PO₄ solution added to increase pH to 6.8 (fine adjustment of pH by using 2 N NaOH and 2 N HCl)
Paddle speed: 75 rpm

TABLE 18

Dissolution Results Example 5

| Media | Time [min] | Sample 1 2.6 mg/cm² [% released] | Sample 2 2.6 mg/cm² [% released] | Sample 3 2.6 mg/cm² [% released] | Sample 1 3.9 mg/cm² [% released] | Sample 2 3.9 mg/cm² [% released] | Sample 3 3.9 mg/cm² [% released] |
|---|---|---|---|---|---|---|---|
| 0.1N HCL | 0 | 0.00 | 0.00 | 0.00 | 0.00 | 0.00 | 0.00 |
| 0.1N HCL | 30 | 0.06 | 0.03 | 0.00 | 0.09 | 0.11 | 0.04 |
| 0.1N HCL | 60 | 0.05 | 0.08 | 0.04 | 0.11 | 0.15 | 0.05 |

TABLE 18-continued

Dissolution Results Example 5

| Media | Time [min] | Sample 1 2.6 mg/cm$^2$ [% released] | Sample 2 2.6 mg/cm$^2$ [% released] | Sample 3 2.6 mg/cm$^2$ [% released] | Sample 1 3.9 mg/cm$^2$ [% released] | Sample 2 3.9 mg/cm$^2$ [% released] | Sample 3 3.9 mg/cm$^2$ [% released] |
|---|---|---|---|---|---|---|---|
| 0.1N HCL | 90 | 0.07 | 0.09 | 0.05 | 0.12 | 0.17 | 0.07 |
| 0.1N HCL | 120 | 0.12 | 0.12 | 0.06 | 0.11 | 0.17 | 0.05 |
| pH 6.8 | 125 | 0.23 | 0.26 | 0.17 | 0.19 | 0.30 | 0.16 |
| pH 6.8 | 130 | 95.59 | 87.88 | 73.04 | 16.93 | 49.07 | 29.61 |
| pH 6.8 | 135 | 99.36 | 99.46 | 96.27 | 96.96 | 78.31 | 89.08 |
| pH 6.8 | 140 | 99.72 | 100.00 | 98.18 | 99.62 | 94.18 | 98.65 |
| pH 6.8 | 150 | 99.86 | 99.96 | 100.18 | 99.77 | 99.73 | 100.00 |
| pH 6.8 | 165 | 99.96 | 100.05 | 100.20 | 99.91 | 100.19 | 99.98 |
| pH 6.8 | 180 | 100.29 | 100.06 | 100.38 | 99.90 | 99.81 | 100.01 |

Examples 6-9—Enteric Coating and Colon Targeting of Pre-Locked Capsules in Fluidized Bed Coater Fluidized Bed Coating Examples and Manual Capsule Filling The EUDRAGIT® polymer(s) were mixed in a container. The Additional excipients were added into the water while gently stirring. After a suitable post stirring time the excipient suspension was added to the polymer dispersion. The spraying suspension was gently stirred during the coating process. The capsules were coated in the pre-locked state utilizing a fluidized bed coater. Afterwards, capsules were manually filled with 200 mg Caffeine and then closed to the final-locked state.

Example 10—Moisture Protection

TABLE 20

Formulation Example 10 - Vcaps® Plus Size 0

| Material | Composition | Solid Composition Percentage |
|---|---|---|
| EUDRAGIT® E PO | 11.1 mg/cm$^2$ | 57.15% |
| Sodium Lauryl sulfate | 10% on ds* | 5.71% |
| Stearic acid | 15% on ds* | 8.57% |
| Talc | 50% on ds* | 28.57% |
| Demineralized Water | On demand | n/a |

TABLE 19

Formulation Example 6-9 - Various Capsule Types

| Example no. | Capsule Size | Capsule Shell | Formula | API | Total solid weight gain % [mg/cm$^2$] | Drug release % of label claim <10% after 2 hrs 0.1N HCl** | % release after 45 min in pH 6.8/ 7.4*** |
|---|---|---|---|---|---|---|---|
| 6 | Size 0 | Pre-locked HPMC | EUDRAGIT® L 30 D-55/ EUDRAGIT® NM 30 D (mixing ratio 9:1) + 10% TEC on ds* Diluent water. solid content 10% w/w | Metoprolol | 5% (0.9) 10% (1.8) 15% (2.7) | Yes Yes Yes | 99% 97% 96% |
| 7 | Size 0 | Pre-locked HPMC | EUDRAGIT® L 30 D-55/ EUDRAGIT® NM 30 D (mixing ratio 7:3) + 10% TEC on ds* Diluent water. solid content 10% w/w | Metoprolol | 10% (1.8) 15% (2.7) | Yes Yes | 97%** 92%** |
| 8 | Size 0 | Pre-locked HPMC | EUDRAGIT® L 30 D-55 + 50% TEC on ds* Diluent water. solid content 10% w/w | Metoprolol | 5% (0.9) 8% (1.5) | Yes Yes | 96% 96% |
| 9 | Size 3 | Pre-locked HPMC | EUDRAGIT® L 30 D-55 + 50% TEC on ds* Diluent water. solid content 10% w/w | Metoprolol Omeprazole | 5% (0.9) 8% (1.2) 8% (1.2) | Yes Yes Yes | 98% 96% 86%** |

*Quantity based on dry polymer substance [%]
**In case of FS 30D, drug release of label claim below 10% after 2 hours in 0.1N HCl followed by 1 hour in pH 6.8
***In case of FS 30D, drug release after 1 hour in pH 7.4 buffer TABLE 20-continued Formulation Example 10 - Vcaps ® Plus Size 0

| Material | Composition | Solid Composition Percentage |
|---|---|---|
| Solid content | 10% w/w[2] | |
| Total solid weight gain | 19.4 mg/cm$^2$ | |

*Quantity based on dry polymer substance [%]

Sodium lauryl sulfate, stearic acid, and EUDRAGIT® E PO are stirred successively into the water, using a dissolver plate, until a yellowish, light turbid solution is obtained which lasts about 1-1.5 h. Talc are added to the polymer solution and homogenized with a dissolver plate for 15 minutes.

Process Parameter

About 70-100 gram pre-locked HPMC capsules were taken and load into fluidized bed coater (Pam Glatt GPCG 1.1) with Wuster assembly.

TABLE 21

Process Parameter Example 10

| Parameter | Value |
|---|---|
| Nozzle bore [mm] | 0.8 |
| Wuster column Height [mm] | 45 |
| Product Temperature [° C.] | 25-30 |
| Inlet air temperature [° C.] | 35-40 |
| Spray rate [g/min] | 1-3 |
| Air flow [CFM] | 25-40 |
| Atomization air pressure [bar] | 1.0-1.2 |

Dissolution:

Method:

Apparatus: ERWEKA DT 700 Paddle Apparatus (USP II)

Detection method: Online UV

Temperature: 37.5° C.

Media I: 700 ml 0.1 N HCL adjusted to pH 1.20 (by using 2 N NaOH and 2 N HCl)

Media II: 700 ml Phosphate buffer adjusted to pH 4.5 (by using 2 N NaOH and 2 N HCl)

Media III: 700 ml Phosphate buffer adjusted to pH 6.8 (by using 2 N NaOH and 2 N HCl)

Paddle speed: 75 rpm

Capsule for dissolution test were coated with 7.2 mg/cm$^2$ total solid weight gain and manually filled with 200 mg caffeine and tested.

TABLE 22

Dissolution Results Example 10

| Time min | 0.1N HCl % Release | SD | Phosphate buffer pH 4.5 % Release | SD | Phosphate buffer pH 6.8 % Release | SD |
|---|---|---|---|---|---|---|
| 0 | 0.0 | 0.0 | 0.0 | 0.0 | 0.0 | 0.0 |
| 15 | 40.9 | 9.9 | 29.1 | 12.8 | 0.2 | 0.0 |
| 30 | 83.5 | 10.7 | 82.5 | 9.1 | 17.0 | 12.7 |
| 45 | 95.6 | 1.5 | 98.4 | 4.2 | 58.7 | 18.0 |
| 60 | 97.5 | 0.3 | 101.3 | 2.3 | 85.5 | 12.3 |
| 90 | 97.6 | 0.5 | 101.2 | 2.3 | 98.8 | 1.5 |
| 120 | 97.8 | 0.4 | 101.3 | 2.3 | 100.6 | 0.7 |

Moisture Uptake Study

EPO coated HPMC capsules filled with and without Silica were stored at 20±2° C./84±5% RH in a desiccator with Potassium chloride supersaturated solution.

TABLE 23

Moisture Uptake Data of coated and uncoated Capsules Filled with Silica.

| Days | Silica alone | HPMC capsule w/o Silica | HPMC capsule w/ Silica | 3 mg/cm$^2$ | 6.6 mg/cm$^2$ | 9.8 mg/cm$^2$ | 13.9 mg/cm$^2$ | 16.7 mg/cm$^2$ | 19.4 mg/cm$^2$ |
|---|---|---|---|---|---|---|---|---|---|
| 0 | 0.00 | 0.00 | 0.00 | 0.00 | 0.00 | 0.00 | 0.00 | 0.00 | 0.00 |
| 1 | 20.31 | 8.06 | 7.93 | 5.06 | 4.36 | 3.46 | 2.09 | 1.65 | 1.42 |
| 2 | 30.86 | 9.68 | 17.05 | 10.14 | 7.90 | 6.02 | 4.54 | 3.77 | 3.25 |
| 3 | 33.59 | 11.29 | 22.72 | 14.02 | 11.44 | 8.28 | 6.17 | 5.36 | 5.07 |
| 4 | 33.59 | 11.29 | 26.49 | 17.90 | 14.09 | 10.83 | 8.08 | 6.95 | 6.11 |
| 7 | 33.59 | 11.29 | 30.27 | 25.96 | 21.16 | 16.50 | 12.44 | 10.66 | 9.76 |
| 8 | 33.59 | 11.29 | 30.27 | 27.75 | 23.23 | 18.20 | 14.07 | 12.24 | 10.81 |
| 9 | 33.59 | 11.29 | 30.27 | 28.34 | 25.00 | 19.90 | 15.16 | 13.30 | 11.85 |
| 10 | 33.59 | 11.29 | 30.27 | 28.34 | 25.88 | 21.04 | 16.52 | 14.36 | 12.89 |
| 11 | 33.59 | 11.29 | 30.27 | 28.34 | 26.18 | 22.17 | 17.34 | 15.16 | 13.67 |
| 14 | 33.59 | 11.29 | 30.27 | 28.34 | 27.94 | 25.29 | 20.33 | 17.80 | 16.28 |
| 15 | 33.59 | 11.29 | 30.27 | 28.64 | 28.24 | 25.57 | 21.42 | 18.60 | 16.80 |
| 17 | 33.59 | 11.29 | 30.27 | 28.94 | 28.53 | 26.99 | 23.05 | 20.45 | 18.63 |
| 18 | 33.59 | 11.29 | 30.27 | 28.94 | 28.53 | 27.27 | 23.60 | 20.98 | 19.67 |

TABLE 24

Moisture Uptake Data of coated and Uncoated Capsules without Silica.

| Days | HPMC capsule w/o Silica | 3 mg/cm² | 6.6 mg/cm² | 9.8 mg/cm² | 13.9 mg/cm² | 16.7 mg/cm² | 19.4 mg/cm² |
|---|---|---|---|---|---|---|---|
| 0 | 0.00 | 0.00 | 0.00 | 0.00 | 0.00 | 0.00 | 0.00 |
| 1 | 8.06 | 8.22 | 7.14 | 5.26 | 4.55 | 4.24 | 3.97 |
| 2 | 9.68 | 9.59 | 9.52 | 6.32 | 5.45 | 5.08 | 4.76 |
| 5 | 11.29 | 9.59 | 9.52 | 7.37 | 7.27 | 6.78 | 6.35 |
| 6 | 11.29 | 9.59 | 9.52 | 7.37 | 7.27 | 6.78 | 6.35 |
| 8 | 11.29 | 9.59 | 9.52 | 7.37 | 7.27 | 6.78 | 6.35 |
| 9 | 11.29 | 9.59 | 9.52 | 7.37 | 7.27 | 6.78 | 6.35 |

The example demonstrate the capabilities of the formulation concept also for moisture protective coatings. Silica filled and locked capsules show significant decrease of the water sorption when stored in a desiccator. This example demonstrates the capabilities of the concept especially for moisture sensitive formulations.

Example 11—Average Gap Width of Vcaps® Plus Hard Shell Capsule

As example, for the whole Vcaps® Plus hard shell capsule size range the gap width between capsule body and cap in the pre-locked or final-locked state was calculated on basis of a value of 100 μm capsule cap wall thickness as described in Capsugel Product Brochure [Dominique Cade; Vcaps® Plus Capsules—A New HPMC Capsule for Optimum Formulation]. The capsule cap wall thickness was subtracted from the external capsule cap diameter getting to the internal capsule cap diameter. In the next step, the capsule cap internal diameter was subtracted from the capsule body external diameter and resulted in the average gap width between capsule body and cap in the pre-locked or final-locked state. The gap width ranges between 25 μm for Vcaps® Plus size 3 and 75 μm for Vcaps® Plus size 00.

TABLE 25

Average Gap Width of Vcaps ® Plus Hard Shell Capsule

| Size | 00el | 00 | 0el | 0el | 0 | 1 | 1el | 2 | 3 | 4 |
|---|---|---|---|---|---|---|---|---|---|---|
| Average Cap Wall Thickness [μm]* | 100 | 100 | 100 | 100 | 100 | 100 | 100 | 100 | 100 | 100 |
| External Diameter | | | | | | | | | | |
| Body [mm] | 8.18 | 8.18 | 7.34 | 7.36 | 7.34 | 6.63 | 6.63 | 6.07 | 5.57 | 5.05 |
| Cap [mm] | 8.53 | 8.53 | 7.65 | 7.66 | 7.64 | 6.91 | 6.91 | 6.35 | 5.82 | 5.32 |
| Gap Width [mμ] | 75 | 75 | 55 | 50 | 50 | 40 | 40 | 40 | 25 | 35 |

*Value from Capsugel Brochure

The invention claimed is:

1. A process for preparing a polymer-coated hard shell capsule, comprising:
   providing a hard shell capsule comprising a body and a cap, in a pre-locked state;
   spray coating said hard shell capsule with a coating solution, suspension or dispersion to form a polymer-coated hard shell capsule;
   separating said body and said cap;
   filling said body with a fill comprising a pharmaceutical or nutraceutical biologically active ingredient; and
   rejoining said body and cap in a final-locked state,
   wherein the polymer-coated hard shell capsule is suitable as a container for pharmaceutical or nutraceutical biologically active ingredients,
   said coating solution, suspension, or dispersion comprises:
   a polymer or a mixture of polymers selected from the group consisting of:
   i) copolymer polymerized from 25 wt. % of methyl methacrylate, 65 wt. % of methyl acrylate and 10 wt. % of methacrylic acid, and a copolymer polymerized from 50 wt. % of ethyl acrylate and 50 wt. % of methacrylic acid;
   ii) a copolymer polymerized from 50 wt. % of ethyl acrylate and 50 wt. % of methacrylic acid;
   iii) a copolymer polymerized from 50 wt. % of ethyl acrylate and 50 wt. % of methacrylic acid, acid a copolymer polymerized from 30 wt. % of methyl methacrylate and 70 wt. % of ethyl acrylate; and
   iv) a copolymer polymerized from 25 wt. % of methyl methacrylate, 25 wt. % of butyl methacrylate and 50 wt. % dimethylaminoethyl methacrylate, and
   a plasticizer selected from the group consisting of alkyl citrates, glycerol esters, alkyl phthalates, alkyl sebacates, sucrose esters, sorbitan esters, diethyl sebacate, dibutyl sebacate, propylene glycol and polyethylene glycol,
   to create a coating layer which covers the outer surface of the polymer-coated hard shell capsule in the pre-locked state and wherein the body and the cap are separable by a conventional capsule filling machine, and
   said coating layer is applied in an amount of from 1 to 8 mg/cm² and has an average thickness of from 5 to 75 μm,
   wherein said coating layer has a moisture protection effect.

2. The process according to claim 1, wherein the polymer-coated hard shell capsule in the pre-locked state is provided to a capsule-filling machine, which performs:
   opening,
   filling with a till comprising:
   a pharmaceutical or a nutraceutical biologically active ingredient, and closing to the final-locked state.

3. The process according to claim 1, wherein a material of the body and the cap is selected from the group consisting of hydroxypropyl methyl cellulose, starch, gelatin, pullulan, and a copolymer of a C1- to C4-alkylester of (meth)acrylic acid and (meth)acrylic acid.

4. The process according to claim 1, wherein the body and the cap comprise:
   encircling notches or dimples in an area where the cap overlaps the body, that allow the capsule to be closed by a snap-into-place mechanism either in the pre-locked state or in the final-locked state.

5. The process according to claim 1, wherein the body comprises:
a tapered rim.

6. The process according to claim 1, wherein the coating layer is applied in an amount of from 1 to 5 mg/cm$^2$.

7. A polymer-coated hard shell capsule, obtained from the process according to claim 1.

8. A process for preparing a polymer-coated hard shell capsule, comprising:
providing a hard shell capsule comprising a body and a cap, in a pre-locked state;
spray coating said hard shell capsule with a coating solution, suspension or dispersion to form a polymer-coated hard shell capsule;
wherein the polymer-coated hard shell capsule is suitable as a container for pharmaceutical or nutraceutical biologically active ingredients,
said coating solution, suspension, or dispersion comprises:
a polymer or a mixture of polymers selected from the group consisting of:
i) a copolymer polymerized from 25 wt. % of methyl methacrylate, 65 wt. % of methyl acrylate and 10 wt. % of methacrylic acid, and a copolymer polymerized from 50 wt. % of ethyl acrylate and 50 wt. % of methacrylic acid;
ii) a copolymer polymerized from 50 wt. of ethyl acrylate and 50 wt. % of methacrylic acid;
iii) a copolymer polymerized from 50 wt. % of ethyl acrylate and 50 wt. % of methacrylic acid, and a copolymer polymerized from 30 wt. % of methyl methacrylate and 70 wt. % of ethyl acrylate; and
iv) a copolymer polymerized from 25 wt. % of methyl methacrylate, 25 wt. % of butyl methacrylate and 50 wt. % dimethylaminoethyl methacrylate, and
a plasticizer selected from the group consisting of alkyl citrates, glycerol esters, allyl phthalates, alkyl sebacates, sucrose esters, sorbitan esters, diethyl sebacate, dibutyl sebacate, propylene glycol and polyethylene glycol,
to create a coating layer which covers the outer surface of the polymer-coated hard shell capsule in the pre-locked state and wherein the body and the cap are separable by a conventional capsule filling machine, and
said coating layer is applied in an amount of from 1 to 8 mg/cm$^2$ and has an average thickness of from 5 to 75 μm,
wherein said coating layer has a moisture protection effect.

* * * * *